United States Patent [19]

Cipolla et al.

[11] Patent Number: 5,451,572
[45] Date of Patent: Sep. 19, 1995

[54] HUMAN RELAXIN FORMULATION

[75] Inventors: David C. Cipolla, Danville; Tue H. Nguyen, San Mateo; Steven J. Shire, Belmont, all of Calif.

[73] Assignee: Genentech, Inc., San Francisco, Calif.

[21] Appl. No.: 50,745

[22] Filed: Apr. 20, 1993

Related U.S. Application Data

[63] Continuation of Ser. No. 303,779, Jan. 27, 1989, abandoned, which is a continuation-in-part of Ser. No. 160,797, Feb. 26, 1988, abandoned.

[51] Int. Cl.⁶ ...................... A61K 38/16; A61K 38/17
[52] U.S. Cl. ......................................... 514/21; 514/12
[58] Field of Search .......................................... 514/12

[56] References Cited

U.S. PATENT DOCUMENTS

| | | | |
|---|---|---|---|
| 2,964,448 | 12/1960 | Anschel | 167/74 |
| 3,003,117 | 10/1961 | Beiler | 424/97 |
| 4,267,101 | 5/1981 | Bigazzi | 260/112 R |
| 4,624,804 | 11/1986 | Voelter et al. | 530/366 |
| 4,758,516 | 7/1988 | Hudson et al. | 435/253 |

FOREIGN PATENT DOCUMENTS

| | | |
|---|---|---|
| 1146069 | 5/1983 | Canada . |
| 0101309 | 2/1984 | European Pat. Off. . |
| 0107782 | 3/1984 | European Pat. Off. ...... C07G 15/00 |
| 0107045 | 5/1984 | European Pat. Off. ...... C07G 15/00 |
| 0260149 | 3/1988 | European Pat. Off. . |
| 3236267 | 4/1984 | Germany . |
| 661662 | 8/1987 | Switzerland ................. A61K 37/24 |

OTHER PUBLICATIONS

Remington's Pharmaceutical Sciences, vol. 15, Dwight L. Deardorff, "Isotonic Solutions", pp. 1405–1418 (1975).
Eduard Eichner, et al. "Relaxin, the Third Ovarian Hormone: Its Experimental Use in Women", (1956), pp. 1035–1048 vol. 71, No. 5 Am. J. Obst. & Gynecology.
R. K. Eldridge, et al., "Rabbit Placental Relaxin: Purification and Immunohistochemical Localization", (1985) pp. 2512–2519 vol. 117, No. 6, *Endocrinology*.
P. A. Fields, et al., "Purification of Relaxin From the Placenta of the Rabbit", (1982) pp. 75–86 380 *Annals New York Acadamy of Sciences*.
Alastair H. MacLennan, et al. "Ripening of the Human Cervix and Induction of Labour with Purified Porcine Relaxin", (1980) pp. 220–223, *The Lancet*.
Alastair H. MacLennan, et al., "Cervical Ripening with Combinations of Vaginal Prostaglandin F2 alpha Estradiol, and Relaxin", Nov. 1981, pp. 601–604, vol. 58, No. 5, *Obstetrics and Gynecology*.
A. H. MacLennan, et al., "The Effect of Procine Relaxin Vaginally Applied at Human Embryo Transfer in an In Vitro Fertilization Programme", (1985) pp. 68–71, 25:68 *Aust. and N.Z. Journal of Obstetrics and Gynaecology*.
Alastair H. MacLennan, et al., "Ripening of the Human Cervix and Induction of Labor with Intracervical Purified Porcine Relaxin" (1986) pp. 598–601, vol. 68, No. 5, *Obstetrics & Gynecology*.
O. David Sherwood, "Relaxin", (1988), pp. 585–673, *The Physiology of Reproduction*, edited by E. Knobil and J. Neill et al. Raven Press, Ltd., New York.
Birnberg and Abitol, "Refined Relaxin and Length of Labor", (1957) pp. 366–370, vol. 10, No. 4, *Obstetrics and Gynecology*.

*Primary Examiner*—Jill Warden
*Assistant Examiner*—Carol A. Salata
*Attorney, Agent, or Firm*—Albert P. Halluin; Pennie & Edmonds

[57] ABSTRACT

A pharmaceutical composition is provided wherein human relaxin is formulated at an acidic pH of about 4 to less than about 7. The composition, useful for effecting parturition and inhibiting premature delivery, includes a buffer capable of maintaining the pH of the composition within a desired range, and may also include an agent to make the composition isotonic, and a stabilizing agent, if necessary. A specific example is human relaxin formulated in a citrate buffer, pH about 5.0, in the presence of sodium chloride, at an ionic strength of about 0.15 $\mu$.

25 Claims, 6 Drawing Sheets

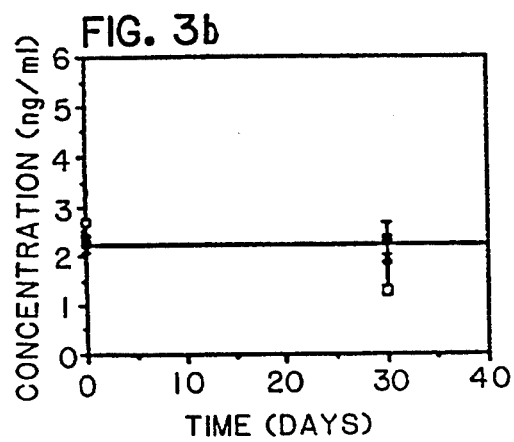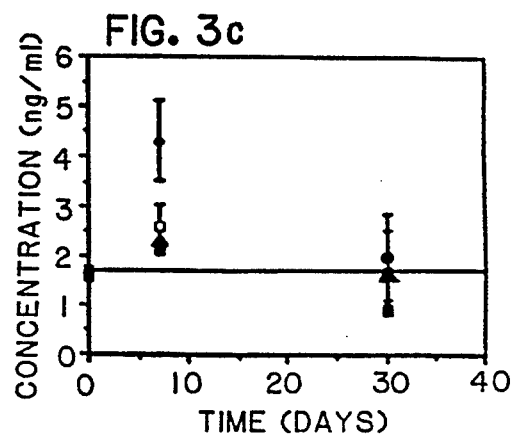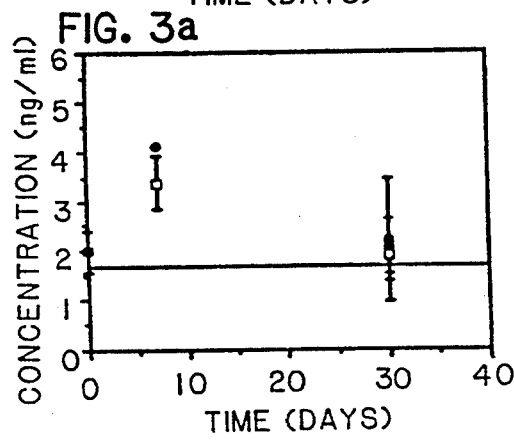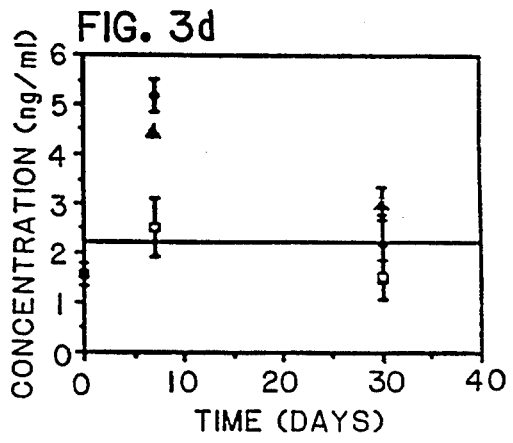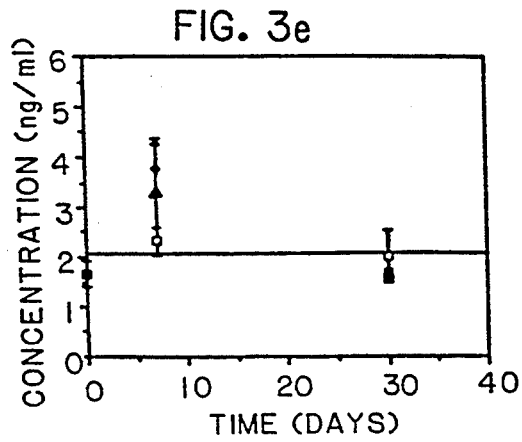

HUMAN RELAXIN FORMULATION

This is a continuation of application Ser. No. 07/303,779 filed on 27 Jan. 1989 now abandoned, which is a continuation-in-part application of U.S. Ser. No. 07/160,797 filed Feb. 26, 1988 now abandoned.

BACKGROUND OF THE INVENTION

1. Field of the Invention

This invention relates to a stable, homogeneous, biologically active human relaxin formulation and to a method of treating mammals with such formulation.

2. Description of the Background Art

Mature human relaxin is an ovarian hormonal peptide of approximately 6000 daltons known to be responsible for remodelling the reproductive tract before parturition, thus facilitating the birth process. Hisaw, F. L., *Pros. Soc. Exp. Biol. Med.*, 23, 661–663 (1926); Schwabe, C. et al., *Biochem. Biophys. Res. Comm.*, 75: 503–570 (1977); James, R. et al., *Nature*, 262: 544–546 (1977). This protein appears to modulate the restructuring of connective tissues in target organs to obtain the required changes in organ structure during pregnancy and parturition. Some of the important roles for relaxin as a pregnancy hormone include inhibition of premature labor and cervical ripening at parturition.

While predominantly a hormone of pregnancy, relaxin has also been detected in the non-pregnant female as well as in the male. Bryant-Greenwood, G. D., *Endocrine Reviews*, 3: 62–90 (1982) and Weiss, G., *Ann. Rev. Physiol.*, 46:43–52 (1984).

Relaxin has been purified from a variety of species including porcine, murine, equine, shark, tiger, rat, dogfish, and human, and shows at least primary and secondary structural homology to insulin and the insulin-like growth factor. In the human, relaxin is found in most abundance in the corpora lutea (CL) of pregnancy.

Two human gene forms have been identified by genomic cloning using probes from the porcine relaxin gene (Hudson, P. et al., *Nature*, 301: 628–631 [1984] and Hudson, P. et al., *The EMBO Journal*, 3: 2333–2339 [1984]), although only one of these gene forms (H2) has been found to be transcribed in CL. It is unclear whether the other gene is expressed at another tissue site, or whether it represents a pseudo-gene. The two human relaxin genes show considerable nucleotide and amino acid homology to each other, particularly in the B and C peptides. However, there are some notable regions of sequence divergence, particularly in the amino-terminal region of both A- and B-chains.

Similar to all species examined, the primary translation product of H2 relaxin is a preprorelaxin consisting of a 24 amino acid signal sequence followed by a B chain of about 29 amino acids, a connecting peptide of 104–107 amino acids, and an A chain of about 24 amino acids.

The fact that H2 relaxin is synthesized and expressed in the ovary suggests that this is the sequence that is involved in the physiology of pregnancy. When synthetic human relaxin (H2) and certain human relaxin analogs were tested for biological activity, the tests revealed a relaxin core necessary for biological activity as well as certain amino acid substitutions for methionine that did not affect biological activity. Johnston et al., in *Peptides: Structure and Function*, Proc. Ninth American Peptide Symposium, Deber, C. M. et al. (eds.) (Pierce Chem. Co. 1985).

Various methods for applying or introducing porcine relaxin as a drug have been published, including intravenous and intramuscular administrations. Birnberg and Abitol, *Obstet. & Gynecol.*, 10: 366–370 (1957); Eichner et al., *Am. J. Obstet. Gyn.*, 71: 1035–1048 (1956). Additionally, porcine relaxin has been used topically in human clinical trials for ripening of the cervix and induction of labor. MacLennan et al., *Obstetrics & Gynecology*, 68: 598–601 (1986); MacLennan et al., *The Lancet*, i:220–223 (1980); MacLennan et al., *Obstetrics & Gynecology*, 58: 601–604 (1981); MacLennan et al., *Aust. NZ J. Obstet Gynaec.*, 25: 68–71 (1985). In these studies the porcine relaxin in distilled water was mixed with water-soluble methylcellulose granules to make a viscous gel. A 2-mg dose was found to improve the cervical score. MacLennan et al. (1981), supra.

In addition, porcine relaxin has been molded into pellets made from polyethylene glycol and used to ripen the human cervix. Evans et al., *Am. J. Obstet. Gynecol.*, 147: 410–414 (1983). Porcine relaxin also has been formulated by suspension in a sterile K-Y gel and phosphate-buffered saline and infused into the cervical os by a sterile insemination pipette. Dilatation of the cervix increased within 8 hours after infusion of 3000 units of relaxin in the cervical os. Perezgrovas and Anderson, *Biology of Reproduction*, 26:765–776 (1982).

European Pat. Publ. No. 86,649 published Aug. 24, 1983 discloses how to prepare porcine preprorelaxin, porcine prorelaxin, and porcine relaxin. Australian Pat. No. 561,670 issued Aug. 26, 1987, European Pat. Publ. No. 68,375 published Jan. 5, 1983, and Haley et al., *DNA*, 1:155–162 (1982) disclose how to prepare porcine relaxin.

European Pat. Publ. No. 101,309 published Feb. 22, 1984 and U.S. Pat. No. 4,758,516 issued Jul. 19, 1988 respectively disclose the molecular cloning and characterization of a gene sequence coding for human H1-relaxin and human H2-relaxin and analogs thereof. European Pat. Publ. No. 260,149 published Mar. 16, 1988 discloses formulations of human prorelaxin. U.S. Pat. No. 4,267,101 issued May 12, 1981 discloses a process for obtaining human relaxin from fetal membranes. European Pat. Publ. No. 251,615 published Jan. 7, 1988 discloses how to combine reduced human relaxin A-chain or analog and reduced human relaxin B-chain or analog under conditions that include a pH greater than about 7.0.

A process for obtaining human relaxin from fetal membranes is disclosed in U.S. Pat. No. 4,267,101. Sherwood, in *The Physiology of Reproduction*, ed. by Knobil and Neill, (New York, Raven Press, 1988), p. 585–673, discloses at p. 587 that almost all of the procedures for extraction and isolation of relaxin take advantage of the stability of relaxin in acidic solvents. In addition, on page 588 it is noted that strongly acidic medium for extraction of relaxin minimizes proteolysis both by the low pH per se and by precipitation of high-molecular-weight proteases. Eldridge and Fields, *Endocrinology*, 117: 2512–2519 (1985) reported that rabbit relaxin has an isoelectric point, as determined by isoelectrofocusing, of about 6.5. This is in contrast to the findings of Fields et al, *Ann. NY Acad. Sci*, 380: 75 (1982), who discovered a much higher isoelectric point for rabbit relaxin.

In addition, copending U.S. application Ser. No. 07/84,255 filed Aug. 10, 1987 discloses in Example 4 dialyzation of refolded relaxin samples into phosphate buffer, Tween 20, or 0.1% acetic acid.

Moreover, U.S. Pat. No. 2,964,448, issued Dec. 13, 1960, discloses injectable relaxin compositions comprising relaxin in an injectable oil, preferably of low acidity, together with a fatty acid salt of aluminum.

It is an object of the present invention to provide a biologically active, stable, homogeneous formulation of human relaxin for use in therapeutic, i.e., topical or parenteral, applications. Another object of this invention is to provide a formulation permitting storage for a long period of time in a liquid state, thereby facilitating storage and shipping prior to administration. Still another object is to reduce aggregation and degradation of human relaxin and to provide a formulation thereof that is resistant to degradation resulting from fluctuations in temperature. Yet another object is the formulation of human relaxin as a gel for cervical applications. A further object is to provide a formulation of human relaxin that has additional therapeutic and physical/chemical advantages.

These and other objects of this invention will be apparent from consideration of this specification as a whole.

SUMMARY OF THE INVENTION

Accordingly, the present invention provides a biologically active pharmaceutical composition useful for modulating the reproductive physiology of mammals, comprising an effective amount of human relaxin in a buffer that maintains the pH of said composition at about 4 to less than about 7, more preferably 4.5-5.5. Additionally, the formulation preferably is isotonic.

The composition may be in a liquid, lyophilizate, frozen liquid, or gel form. If the composition is in the form of a gel, it preferably further comprises a water-soluble polysaccharide or polyethylene glycol, most preferably methylcellulose.

In another embodiment, this invention relates to a method of modulating the reproductive physiology of mammals comprising administering to the mammal a therapeutically effective amount of the composition herein.

It was not appreciated until this invention that under acidic conditions the degradation rates of human relaxin as assessed by HPLC are slower at an optimal level. Therefore, the immunogenicity of the formulation may be reduced, and its safety improved. As a result of this finding, formulation of human relaxin can be prepared that retains biological activity, has a long shelf-life, and can be administered therapeutically with or without lyophilization. Preferably the relaxin is formulated at approximately pH 5 with a shelf-life (assuming an acceptable reduction of 10% in the HPLC main peak area) at 5° C. of at least 2 years.

BRIEF DESCRIPTION OF THE DRAWINGS

FIGS. 3a-3e represent graphs of the activity of human relaxin as a function of time for five different formulations ranging from pH 3 to 7.5 at three different temperatures.

DESCRIPTION OF THE PREFERRED EMBODIMENTS

Figure 1A:
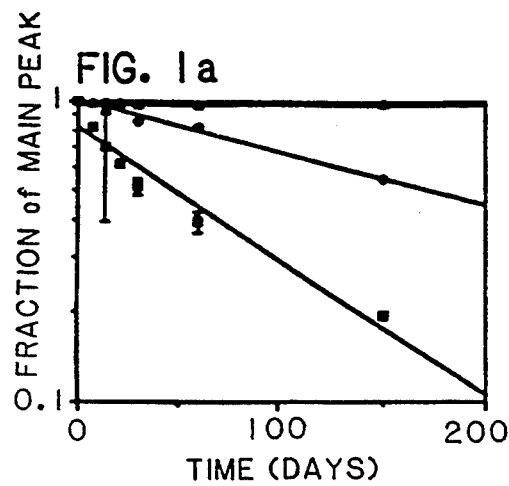
FIGS. 1a-1e represent graphs of the fraction of the main RP-HPLC peak for human relaxin as a function of time for five different formulations ranging from pH 3 to 7.5 at three different temperatures.

As used herein, human relaxin denotes a functional protein having specific hormonal functions, such as, for example, the modulation of the reproductive physiology of human beings and possibly other mammals, including, but not limited to, maintaining pregnancy, effecting parturition, and enhancing sperm motility as an aid in fertilization. As specific examples of such uses are included performing numerous reproductive functions relating to pregnancy as well as other biological functions such as preparation of the birth canal by, for example, effects on the pubic symphysis, or pubic ligament, and rearrangement of collagenous filaments thus effecting parturition; depressant effects on the myometrium; preparation of the endometrium for implantation; role in luteolysis; growth and differentiation of the mammary glands; enhancement of sperm motility; and possible augmentation of the ability of sperm to penetrate the human cervix. The functionality of human relaxin or variants thereof is assayed by whether there is a positive effect in the murine pubic symphysis in vitro bioassay or an increase in cAMP levels in an in Vitro assay using a uterine cell line. The term "biologically active" to define pharmaceutical compositions herein is used in the context set forth above for human relaxin.

Human relaxin and its methods of preparation, including synthesis in recombinant cell culture, are known (e.g., EP 101,309 and 112,149, equivilent to U.S. Pat. No. 4,758,516 supra the disclosures of which are incorporated herein by reference).

Included within the scope of the term "relaxin" are human relaxins from recombinant or native sources as well as relaxin variants, such as amino acid sequence variants. It has been found by mass spectroscopic ionization using fast-atom bombardment that the predominant species of human relaxin in the corpus luteum and serum is the H2 relaxin form with a truncated B chain, i.e., relaxin H2(B29 A24), wherein the four C-terminal amino acids of the B-chain are absent so that the B-chain ends with a serine at position 29. This predominant form (designated herein as "short relaxin" as opposed to the "long relaxin" containing a B chain of 33 amino acids) is preferred for use herein.

Also included within the scope of the term "human relaxin" are other insertions, substitutions, or deletions of one or more amino acid residues, glycosylation variants, unglycosylated human relaxin, organic and inorganic salts, covalently modified derivatives of human relaxin, human preprorelaxin, and human prorelaxin. Through the use of recombinant DNA technology, relaxin variants may be prepared by altering the underlying DNA. All such variations or alterations in the structure of the relaxin molecule resulting in variants are included within the scope of this invention so long as the functional (biological) activity of the human relaxin is maintained. Those variants of human relaxin having the described functional activity can be readily identified using the in vitro assays mentioned above.

One particular variant that is useful herein is described in copending U.S. application Ser. No. 07/84,255, supra, filed Aug. 10, 1987, the disclosure of which is incorporated herein by reference. This variant is prepared from relaxin-encoding sequences that are altered in one or more ways to introduce aspartic-acid-encoding codons at specific position(s) within the selected gene. The resulting variant proteins may be treated with dilute acid to release a desired protein or peptide, thereby rendering the protein more isolable and purifiable.

Copending U.S. Ser. No. 07/284,281, filed Dec. 14, 1988, the disclosure of which is incorporated herein by reference, discloses the preparation of relaxin by producing a fusion protein of a relaxin chain and ubiquitin and using a ubiquitin hydrolase to cleave the protein. In addition, a yeast expression system for prorelaxin using a vector encoding trans-activating protein is described in U.S. Ser. No. 07/071,674, filed Sep. 25, 1987, the disclosure of which is incorporated herein by reference.

The relaxin herein may be prepared by synthesis of the A and B chains, and purification and assembly thereof, as described in EP 251,615, published Jan. 7, 1988, the disclosure of which is incorporated herein by reference, and U.S. Ser. No. 07/084,255 filed Aug. 10, 1987, supra. For synthetic relaxin, a 4:1 molar ratio of A to B chain is generally employed. The resulting product is then purified by any means known to one of ordinary skill in the art, including, for example, reverse-phase HPLC, ion exchange chromatography, gel filtration, dialysis, or the like, or any combination of such procedures.

The effective amount of relaxin to be formulated in the composition is selected based on several variables, including the specific condition being treated, the patient's medical history, and the therapeutic route and schedule being utilized. Conditions being treated include difficult delivery of a term fetus, inhibition of premature labor, and treatment of certain connective tissue disorders such as scleroderma. The therapeutic route includes parenteral administration, such as, e.g., subcutaneous, intraperitoneal, intravenous, and intramuscular administration.

The average current dosage for the treatment of a problem pregnancy varies depending on numerous indicia known to the ordinarily skilled physician, including the route and scheduling of administration, the stage of gestation, the type of relaxin, the condition of the patient being treated, the form of the composition, and such other considerations as would be known to the physician. As an example, in the clinic, the effective amount for topical administration is suitably about 5 to 10 ml of gel containing about 1 to 3 mg of human relaxin. The average doses administered intravenously are in the range of about 0.1 $\mu$g per kilogram to 1500 mg per kilogram for effecting reproductive functions such as preparation of the birth canal.

The pH of the formulation is maintained at about 4 to less than about 7, more preferably about 4 to 6, still more preferably about 4.5 to 5.5, and most preferably about 5. The optimum pH in turn will depend on the ionic strength and storage temperature of the formulation. The formulation is preferably isotonic, and preferably the ionic strength of the formulation is at least about 0.1 $\mu$, more preferably about 0.1 to 0.2 $\mu$, most preferably about 0.15 $\mu$, and the osmolality of the formulation is preferably about 200 to 300 mmol/kg, more preferably about 240–260 mmol/kg. If the storage temperature is about 40° C., the pH is preferably about 4 to less than about 7. If the storage temperature is about 25° C., the pH is preferably about 4 to 5.

Preferably the pH of the formulation herein is maintained by use of a buffer capable of maintaining the pH within the desired range. Whether a particular buffer can be employed will depend on its buffer capacity, and more specifically on its pK value. Examples include certain organic acid buffers and histidine. Suitable organic acid buffers (buffers of organic acids and salts thereof) include, e.g., citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), malate buffers, gluconate buffers (e.g., gluconic acid-sodium gluconate mixture, gluconic acid-sodium hydroxide mixture, gluconic acid-potassium gluconate mixture, etc.), borate buffers, imidazole buffers, lactate buffers (e.g., lactic acid-sodium lactate mixture, lactic acid-sodium hydroxide mixture, lactic acid-potassium lactate mixture, etc.), and acetate buffers (e.g., acetic acid-sodium acetate mixture, acetic acid-sodium hydroxide mixture, etc.). The most preferred buffers herein are citrate and acetate buffers, most preferably citrate. It is noteworthy that buffers such as phosphate and Tris buffers that have been used traditionally do not maintain the pH of the formulation at the desired level.

The formulation herein preferably has the proper isotonicity and osmolality so as to be useful for parenteral applications, particularly intravenous. If the ionic strength and osmolality are not within the preferred ranges mentioned above and it is desirable to adjust it to those ranges, an agent may be added to the formulation that adjusts the osmolality appropriately. Such agents include, for example, alkali metal salts and alkali earth metal salts such as halides, for example, sodium and potassium chloride, magnesium bromide, etc., and neutral polyhydric sugar alcohols such as mannitol. The most preferred agent is sodium chloride.

A pharmaceutically acceptable agent for stabilizing and lyophilizing the formulation may also be added to the formulation. Examples include polyhydric sugar alcohols such as trihydric or higher alcohols, most preferably glycerin, erythritol, glycerol, arabitol, xylitol, sorbitol, and mannitol, as well as straight-chain alcohols such as, e.g., ethanol and propylene glycol. These agents can be used alone or in a combination thereof. Preferably the agent is formulated in an amount of about 1 to 25% by weight, and preferably 2 to 10% by weight, taking into account the amounts of the other ingredients.

In addition, the composition herein suitably contains an agent to enhance absorption by the cervix or vagina if the preparation is topical. Examples of such absorption enhancers include molecules that have a structure similar to that of cholesterol, such as glycocholate, e.g., sodium glycocholate, cholate, e.g., sodium cholate, and fusidic acid and its derivatives, including salts and esters such as tour-24,25dihydrofusilate non-ionic surfactants;

derivatives of fatty acids having about 7 to 25 carbon atoms, such as oleic acid; niacinamide; nicotinic or salicylic acid, or their salts or esters; and azone.

The preferred liquid composition herein is human relaxin, in a 10 mM citrate buffer at pH 5, with sodium chloride present to a total ionic strength of about 0.15 $\mu$, representing the proper osmolality.

The formulation herein may be in liquid, frozen, or gel form, or may be lyophilized and reconstituted. One skilled in the art will be able to determine the type and amount of any additional excipient, such as a sugar alcohol, that might be necessary to optimize lyophilization. Mannitol is one such preferred additive. The formulation herein is stable for prolonged periods of time and may be stored in a liquid state at various temperatures. Preferably, the liquid formulation is stored in glass rather than plastic. In addition, the formulation may be frozen, thawed, refrozen, and rethawed without adverse effect. A preferred storage temperature is in the range of −20° to 30° C., with a most preferred storage temperature range of about 2° to 8° C. The formulation herein in liquid form will retain biological activity for at least 30 days and physical stability for at least 2 years as extrapolated from 1-year data.

For obtaining a gel formulation, the liquid composition is typically mixed with an effective amount of a water-soluble polysaccharide or polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullulan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too fluid or viscous, and will not destabilize the relaxin held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400–600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2–5% of the gel and the relaxin is present in an amount of about 100–1000 $\mu$g per ml of gel. More preferably, the methylcellulose comprises about 3% of the gel and the amount of relaxin is about 300–1000 $\mu$g per ml of gel.

Also, if the formulation is a gel that is light sensitive, preferably it contains one or more agents such as antioxidants, preferably ascorbic acid (preferably at least 0.5%), and/or co-solvents, preferably glycerol and/or ethanol (preferably at about 20%), most preferably glycerol, to inhibit or prevent photo-oxidation if the gel is exposed to light. For example, the methylcellulose gel is stored in a foil-covered or colored vial to prevent light from entering.

The following examples illustrate the present invention, but are not to be construed to limit the scope of the invention. All patent and literature citations herein are incorporated expressly by reference.

EXAMPLE I

Human relaxin stability studies were conducted in several 10 mM buffers ranging from pH 3 to 10 (Study 1). The effects of increasing ionic strength on the stability of the formulations were also investigated (Study 2).

Sample Preparation

For Studies 1 and 2, the human long relaxin (H2 form with B chain of 33 amino acids) was obtained by synthesizing the A and B chains (disclosed in EP 112,149, supra) using the solid-phase synthetic methodology of Barany, G. and Merrifield et al.,(1980) in *The Peptides*, 2: 1–284, Gross, E. and Meienhofer, J., eds., Academic Press, New York. The chains were HPLC purified (trifluoroacetic acid (TFA)/acetonitrile gradient), and assembled in a 4:1 weight ratio of A:B chain at pH about 10.2 in 0.2–1M CAPS buffer (3-[cyclohexylamino]propanesulfonic acid, Calbiochem), 0.75 M guanidine hydrochloride, 10% (v/v) methanol (Burdick and Jackson), and a range of total protein of from 0.25 to 2.0 mg/ml. The solution was thoroughly purged with nitrogen and stirred overnight (12–18 hours) at 20° C. The sample is then dialyzed into an appropriate buffer (phosphate buffered saline, 0.01% Tween 20, or 0.1% acetic acid) and applied to a Vydac C-4 HPLC column using a TFA/acetonitrile gradient. The relaxin fraction was identified on HPLC and collected in a TFA buffer that was vacuumed off the sample. The relaxin thus obtained was lyophilized.

124 mg (about 80% by weight as peptide) of the long relaxin was employed for Study 1 and 20 mg (about 67% by weight of peptide) for Study 2. Both samples were white lyophilized powders with up to 15% by weight of trifluoroacetic acid (TFA). Sufficient Milli-Q water (deionized water that has been passed through a water purification system consisting of activated charcoal and ion exchanges manufactured by Millipore Inc.) was added to obtain a concentration of about 1 mg/ml of peptide.

The long relaxin in Milli-Q water was exchanged into the appropriate formulation buffer system by dialysis at 5° C. using Spectrapor 7 (3500 MW cutoff) dialysis tubing. This tubing was precleaned in 2 liters of Milli-Q water containing 1 ml $\beta$-mercaptoethanol, 3.36 g EDTA, and 4.2 g NaHCO$_3$ followed by four washes in 2 liters of Milli-Q water at 60° to 70° C. The tubing was subsequently stored in 50% (w/v) ethanol at 5° C. and washed extensively before dialysis.

Concentrations of all samples immediately after dialysis were determined by ultraviolet absorption spectroscopy using an extinction coefficient of 2.18 $(mg/ml)^{-1}cm^{-1}$ as determined by quantitative amino acid analysis on an analog of relaxin where methionine residues were replaced by lysine residues, correcting the concentrations for effects of light scattering. Each sample was sterile filtered in a laminar flow hood through 0.2 μ Millex GV-4 (0.01 sq. inches surface area) filters into sterile 100 μL, 300 μL, or 1.5 ml borosilicate glass vials (Wheaton) with Teflon-lined screw caps and stored at 5, 25, and 40° C. The concentrations are accurate indications of what was filtered into the vials, because separate experiments indicated that filtration at 1 mg/ml did not result in significant lowering of the protein concentration.

In Study 1 triplicate vials for each buffer were stored at each temperature to obtain error estimates and to determine if samples were contaminated upon repetitive sampling from the same vial.

For Study 3, the relaxin H2(B33 A24) $_4$pyro-Glu$^1$ was employed, wherein H2 refers to the human gene expressed in the human ovary, A and B refer to the respective chains of human relaxin, the numbers following A or B refer to the length of the chain, i.e., number of amino acids comprising the A- or B-chain, and the subscript preceding the amine acid designates the A- or B-chain in which the amino acid is located and the superscript following the amino acid refers to the position in the chain. Preparation of this analog and recombination of the chains are described generally in EP Pub. No. 251,615, supra. The protein was purified as described above for Studies 1 and 2.

About 36 ml of the human pyroglu relaxin at about 4.65 mg/ml was formulated in 10 mM citrate at pH 5.0 as described above and made isotonic by addition of NaCl. This protein was diluted to 1 mg/ml (determined spectrophotometrically using an extinction coefficient of 2.18). A total of 1.4 ml of each formulation was sterile filtered in a laminar flow hood into 1.5-ml autoclaved glass vials equipped with Teflon stoppers. In a study of freezing and freeze-thaw effects, the protein was also diluted to 2 mg/ml and frozen, and then studies were performed.

Stability Protocol

Study 1: Twenty-ml portions of long relaxin at about 1 mg/ml in water were exchanged by dialysis into 10 mM glycine (pH 3), 10 mM citrate (pH 5), 10 mM acetate (pH 5), 10 mM histidine (pH 6), and 10 mM Tris buffer (pH 7.5), with the exact compositions provided in Table I, with the citrate buffer ingredients calculated to give a pH of 5.0. All buffers were made up to isotonicity (0.154 μ) with the addition of NaCl. Concentrations were determined as previously described, samples sterile filtered, and vials filled according to the protocol shown in Table II. The resulting 135 100-μL-microvials and 90 1.5-ml-vials were placed on stability tests at 5, 25 and 40° C. Samples were assayed at 0, 7, 21, and 30 days by reverse phase HPLC, ELISA, and cyclic AMP assays. In addition to these assays, the samples were also assayed by near UV circular dichroism (near UV CD) and analytical ultracentrifugation (UC) on days 0 and 30. In addition, the citrate formulation was analyzed for five months by RP-HPLC at 5° C. and for sixty days by RP-HPLC at −20° C.

Study 2: One-ml portions of the long relaxin at about 1 mg/ml in water were exchanged by dialysis into 10 mM acetate, citrate, and succinate buffers at pH 5 with no additional salt, 0.1M or 0.5M NaCl (buffer compositions given in Table I). The resulting nine samples were each sterile filtered, divided into three equal volumes, and loaded into sterile 300 μL glass microvials. The resulting 27 vials containing about 9 mg were placed on stability testing at 5, 25, and 40° C. for up to 40 days. Samples were assayed by an ELISA assay and a C4 reverse-phase HPLC assay on days 0, 7, 14, 28, and 40. The remaining 3 mg of relaxin was kept in Milli-Q water at 5° C. and used as the reference material. The results in Study 1 and in subsequent stability studies showed this relaxin in water to be stable by reverse phase HPLC for at least five months at 5° C. These observations were repeated on reference samples used in subsequent stability studies.

TABLE I

PROTOTYPE LIQUID FORMULATIONS FOR RELAXIN AT 1.0 MG/ML

| Formulation | Composition per ml |
|---|---|
| FORMULATIONS FOR STUDY 1 | |
| 10 mM Glycine, pH 3.0 | 0.74 mg Glycine-HCl (6.66 mM) |
|  | 0.25 mg Glycine (3.34 mM) |
|  | 8.87 mg NaCl (0.152M) |
| 10 mM Acetate, pH 5.0 | 0.25 mg Sodium Acetate (2.96 mM) |
|  | 7.0 uL 1.0M Acetic Acid (7.04 mM) |
|  | 8.60 mg NaCl (0.147M) |
| 10 mM Citrate, pH 5.0 | 0.69 mg Citric Acid Monohydrate (3.3 mM) |
|  | 1.97 mg Sodium Citrate Dihydrate (6.7 mM) |
|  | 7.25 mg NaCl (0.124M) |
| 10 mM Histidine, pH 6.0 | 1.12 mg Histidine-HCL (5.32 mM) |
|  | 0.73 mg Histidine (4.68 mM) |
|  | 8.66 mg NaCl (0.148M) |
| 10 mM Tris, pH 7.5 | 1.32 mg Tris-HCl (8.36 mM) |
|  | 0.20 mg Tris Base (1.64 mM) |
|  | 8.52 mg NaCl (0.146 mM) |
| FORMULATIONS FOR STUDY 2 | |
| 10 mM Acetate, pH 5.0 | 0.54 mg Sodium Acetate (3.42 mM) |
|  | 3.42 μL 1.0M Acetic Acid (6.58 mM) |
| 10 mM Succinate, pH 5.0 | 0.51 mg Succinic Acid (4.25 mM) |
|  | 1.55 mg Disodium Succinate Hexahydrate (5.75 mM) |
| 10 mM Citrate, pH 5.0 | 0.53 mg Citric Acid (2.78 mM) |
|  | 2.12 mg Sodium Citrate Dihydrate (7.22 mM) |
| All 3 buffers + 0.1M NaCl | 5.84 mg NaCl |
| All 3 buffers + 0.5M NaCl | 29.22 mg NaCl |

*All formulations are isotonic (0.154 μ, the remaining ionic strength made up via addition of NaCl)

TABLE II

VOLUME (μL) OF FORMULATION PER VIAL REQUIRED FOR EACH ASSAY FOR RELAXIN STABILITY STUDY 1

| time | ELISA | UV | HPLC | Cyclic AMP | Near UV CD | UC |
|---|---|---|---|---|---|---|
| 0 day | 10 | 100 | 10 | 10 | 500 | 50 |
| 7 day | 10 | — | 10 | 10 | — | — |
| 14 days | 10 | — | 10 | 10 | — | — |
| 21 days | 10 | — | 10 | 10 | — | — |
| 1 mnth | 10 | 100 | 10 | 10 | 500 | 50 |
| 2 mnths | 10 | 100 | 10 | 10 | 500 | 50 |
| 3 mnths | 10 | 100 | 10 | 10 | 500 | 50 |
| 4 mnths | 10 | 100 | 10 | 10 | 500 | 50 |
| 5 mnths | 10 | 100 | 10 | 10 | 500 | 50 |
| 6 mnths | 10 | 100 | 10 | 10 | 500 | 50 |

100 μL of formulated protein for 7−14− and 21− day ELISA, HPLC, and cyclic AMP assays was placed into sterile 100 μL microvials (3 vials/assay×5 formulations×3 temperatures=45 vials). The 1-, 2- and 3-month samples were grouped in a similar manner (45 vials), and the 4-, 5- and 6-month samples were grouped similarly for an additional 45 vials, resulting in 135 100-μL vials for these three assays. The remaining formulated protein was dispersed into 1.5-ml vials so that each vial contained 0.9 ml, which was sufficient volume for the CD, UV and UC assays. This resulted in a total of 90 1.5-ml vials (5 formulations×3 temperatures×6 time points).

Study 3: The formulations with the relaxin analog to be evaluated were as follows:
1. 10 mM citrate buffer made isotonic with NaCl
2. 10 mM citrate buffer made isotonic with NaCl dialyzed against a freshly prepared isotonic citrate buffer. (This serves as a control.)
3. 10 mM citrate buffer made isotonic with mannitol (5.07%) dialyzed against a 10 mM citrate, 5.07% mannitol buffer (no NaCl)
4. 10 mM citrate buffer made isotonic with NaCl to which was added 5% absolute ethanol
5. 10 mM citrate buffer made isotonic with NaCl to which was added 10% absolute ethanol
6. 10 mM citrate buffer made isotonic with NaCl to which was added 5% glycerol
7. 10 mM citrate buffer made isotonic with NaCl to which was added 10% glycerol
8. 10 mM citrate buffer made isotonic with NaCl to which was added 5% propylene glycol
9. 10 mM citrate buffer made isotonic with NaCl to which was added 10% propylene glycol
10. 10 mM citrate buffer made isotonic with NaCl to which was added 0.02% EDTA (disodium salt)
11. 10 mM citrate buffer made isotonic with NaCl to which was added 5% mannitol These formulations were placed in triplicate at 5, 25, and 40° C.

In addition, 1 ml of relaxin at 2 mg/ml in original isotonic (NaCl) citrate buffer was sterile filled into each of 27 1.5-ml vials and frozen at −20° C. At day 0, 3 vials were thawed and assayed; on subsequent days three vials were thawed and assayed.

Assay Methods

HPLC Assay: Chromatograms were obtained on a Vydac TM C4 reverse phase column using the following column conditions: 1 ml/min. flow rate, solution A: 0.1% TFA, solution B: 0.1% TFA, 90% acetonitrile, gradient of 20% A to 50% B at 1% /minute.

In Study 1 the total areas of the chromatograms remained constant within the error of the measurements, i.e., the decrease in the area of the main peak was accounted for by an increase in the areas of side peaks. Subsequent regeneration of the HPLC column revealed that most of the relaxin eluted under the conditions of the gradient. This behavior is in contrast to what was observed in Study 2, where the total area determined by HPLC assay was not constant with time. As the material was purified to a greater degree, the stability as measured by HPLC improved.

ELISA Assay: Samples were diluted into the diluent buffer for ELISA assays so that the expected concentration would fall in the midrange of the linear portion of the standard curve. The primary antibody for the ELISA assay is an affinity-purified rabbit polyclonal antibody raised against the synthetic human relaxin peptide wherein the human relaxin A-chain has a pyro-Glu at position 1 of the chain.

Concentrations as determined by ELISA were normalized by a reference that was submitted along with the stability samples. The values determined by the ELISA were usually greater than the values expected based on UV spectroscopy, but after normalizing, were about 20% lower than the expected values. In Study 1 triplicate samples were submitted for each time point by diluting samples from each of the three vials.

Cyclic AMP Assay: Samples were diluted in a cell assay buffer and were incubated with Rhesus Monkey uterine cells. The resulting cell suspension was assayed for cyclic AMP using the manufacturer's assay procedure of dupont de Nemours, Inc., Wilmington, Del. A standard curve was used to relate cyclic AMP concentration to relaxin concentration. This concentration theoretically is a "bioactive" concentration in contrast to the ELISA, which measures an "immune reactive" concentration. A reference sample at known concentration was submitted along with stability samples and used to normalize the determined concentrations of relaxin.

Mouse Pubic Symphysis Assay: The murine pubic symphysis ligament in vivo bioassay measures the remodeling effect of relaxin on connective tissue. See Steinetz, B. G. et al. (1960) *Endocrinology*, 67: 102.

Near UV Circular Dichroism: Relaxin samples at about 1 mg/ml were diluted 1:1 with dialyzate and spectra obtained in a 0.5 cm pathlength thermostated cylindrical cuvette at 20° C. from 320 to 240 run in an Aviv TM modified Gary 60 spectropolarimeter. After collection of the CD data the sample was removed from the CD cell and diluted five-fold into phosphate-buffered saline. The concentration was then determined as before using UV absorption spectroscopy. The CD signal in ellipticity (millidegrees) was converted to mean residue weight ellipticity in the manner described by Adler et al., *Meth. Enzym.*, 27: 675 (1973) using a mean residue weight of 112.9 g for human relaxin.

Analytical Ultracentrifugation: Relaxin stability samples were diluted four-fold with the appropriate dialyzate and loaded into double-sector ultracentrifuge cells, which were placed into an An-F 4 hole analytical rotor. Centrifugation was performed in a Beckman Model E analytical ultracentrifuge at 32,000 rpm at 20.0° C. for 18 hours. In separate experiments it was determined that 18 hours was sufficient time to obtain sedimentation equilibrium. The concentration gradient in the cell was determined by UV absorption at 280 nm using a photoelectric optical scanner. The curve traces were inputted into a Macintosh computer using a Macintizer TM tracing pad. The weight average molecular weight is related to the concentration gradient in the cell using the equation (Teller, *Meth. Enzym.*, 27:346 [1972]):

$$M_w = 2RT/[w^2(1-vp)]dlnc/dr^2,$$

where $M_w$ is weight average molecular weight, T is temperature, R is the gas constant, w is the angular velocity in radians, v is the partial specific volume of the protein, p is the solution density, c is the protein concentration, and r is the radial distance from the center of rotation. The equation assumes an ideal solution and appears to be appropriate for relaxin sedimentation under the buffer conditions chosen. Least squares regression analysis of the lnc versus $r^2$ yields the weight average molecular weight as an average over the concentration range in the cell. The data were also smoothed with a third-order polynomial and the values for $dlnc/dr^2$ obtained at each concentration measured in the centrifuge cell. The partial specific volume of 0.731 ml/g for relaxin was computed from the amino acid composition using values for the individual amino acid residues in accordance with Cohn and Edsall, "Proteins, Amino Acids and Peptides as Ions and Dipolar Ions" (Hafner: New York, 1965), pp. 157–175.

Results

Figure 1B:
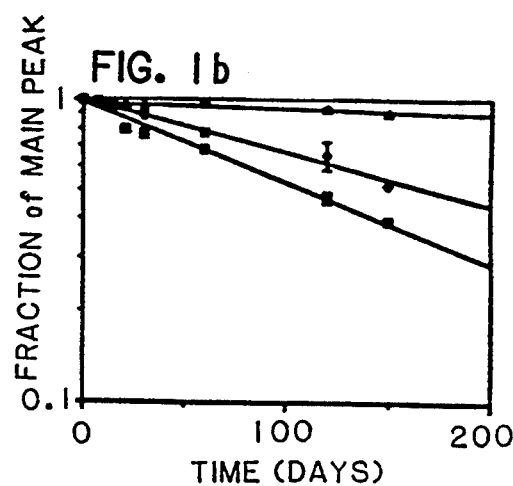
Figure 1C:
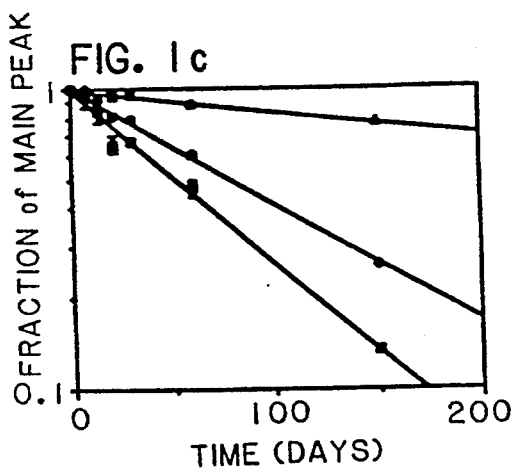
Figure 1D:
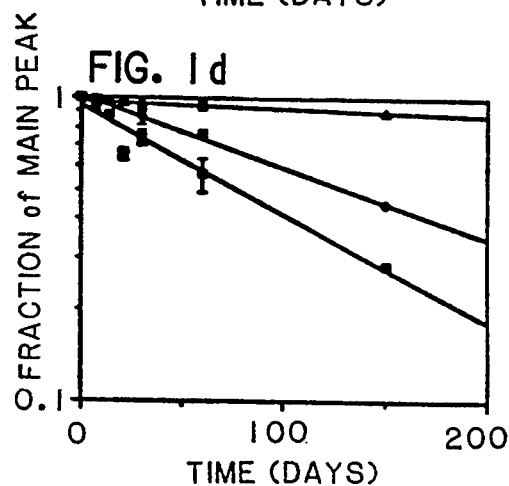
Figure 1E:
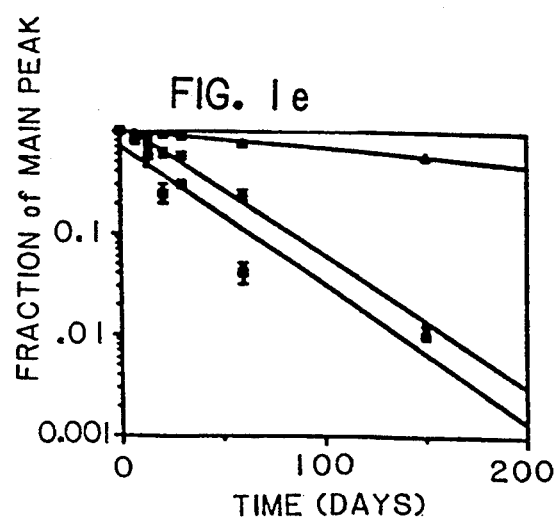
Figure 2:
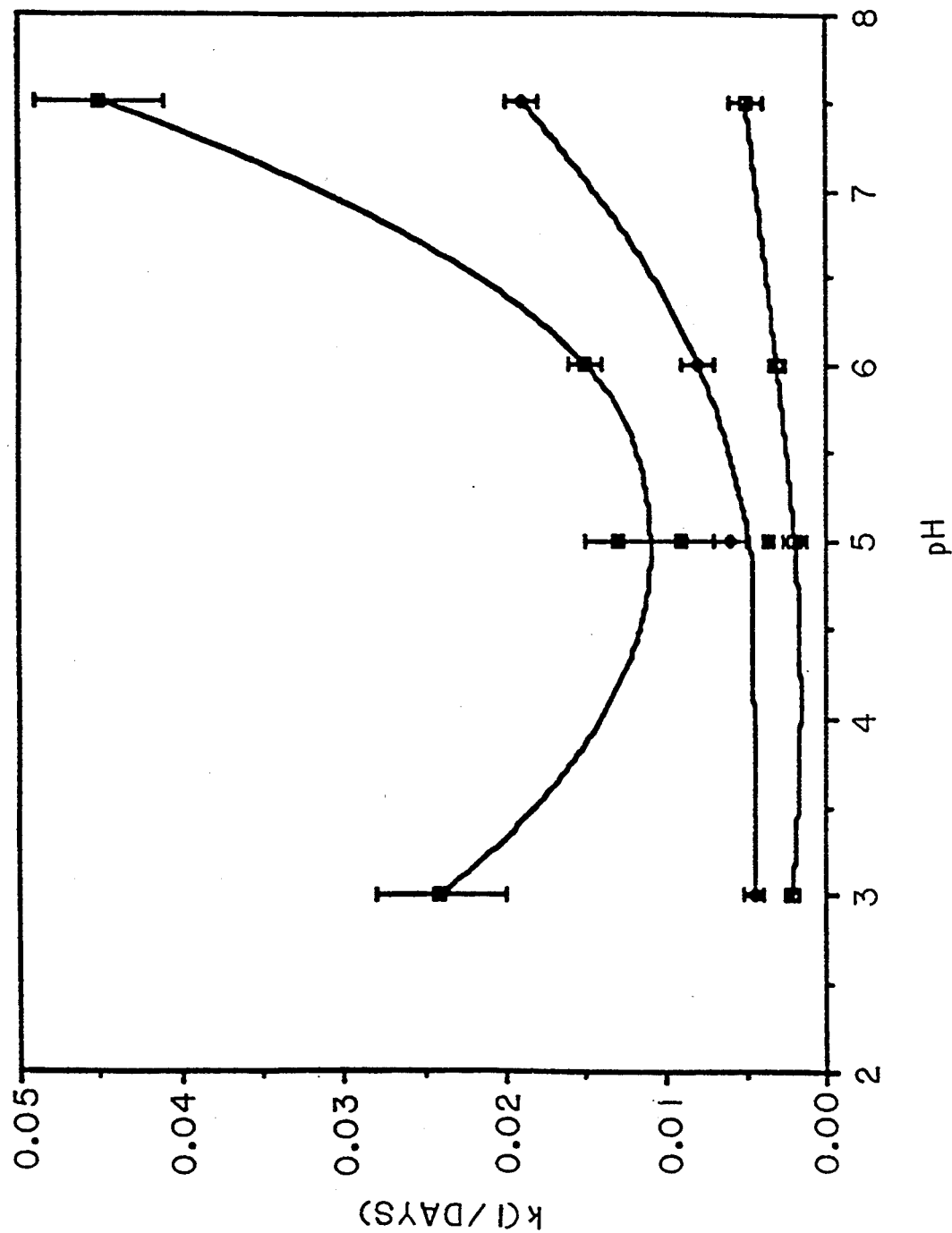
FIG. 2 represents a graph of the rate of degradation of human relaxin formulations as a function of the pH of the formulation, as measured by RP-HPLC at three different temperatures.

Study 1: The degradation of relaxin as a function of time was monitored by reverse phase HPLC. As the total area of all the HPLC peaks remained constant over time, the percentage of the total area was used to investigate the kinetics of relaxin degradation. The fraction of the main peak remaining was computed from triplicate samples (when available), and first-order plots of the degradation kinetics of the main HPLG peak for the five formulations shown in Table I (ranging from 3.0 to 7.5) were determined. The kinetics were followed by measuring the rate of disappearance of relaxin main peak by reverse phase HPLC. FIGS. 1a–1e are graphs of the fraction of the main HPLC peak versus time for the five formulations at these three temperatures, indicating rate of degradation. FIG. 1a is relaxin in 10 mM glycine (pH 3.0), FIG. 1b is relaxin in 10 mM citrate (pH 5.0), FIG. 1c is relaxin in 10 mM histidine (pH 6.0), FIG. 1d is relaxin in 10 mM acetate (pH 5.0), and FIG. 1e is relaxin in 10 mM Tris (pH 7.5). In each graph, the triangles indicate 5° C., the circles 25° C., and the squares 40° C. These figures show that relaxin degradation can be analyzed by first-order rate kinetic analysis. FIG. 2 shows the plot of the determined first order rate constants for degradation of the main peak versus pH for the five formulations at 5 (open squares), 25 (diamonds), and 40° C. (solid squares). The data in FIG. 2 show that human relaxin is most stable at a pH of about 4 to 6, and most particularly at pH 5.

Study 2: In the succinate, acetate, and citrate formulations, the stability of relaxin as measured by RP-HPLC and ELISA is not significantly affected by variations in ionic strength as obtained by using 0.0M, 0.1M, and 0.5M NaCl. The protein was formulated at about 0.15 μ ionic strength at an osmolality of about 250 mmol/kg in order to be able to use the formulation for intravenous as well as intramuscular injection.

Study 3: Tables III and IV show, respectively, the reverse phase HPLC data regarding the citrate formulation at pH 5.0 stored at 5° C. for 1 year (at 1 mg/ml concentration of relaxin) and at −20° C. for 60 days (at 2 mg/ml concentration of relaxin). The data in Table III can be extrapolated to estimate stability at 5° C. for at least 2.0 years (i.e., no more than about 10% degradation), assuming first-order kinetics. Both tables indicate that the formulations are stable at the respective temperatures.

TABLE III

REVERSE PHASE HPLC STABILITY OF CITRATE FORMULATION STORED AT 5° C.

| Time (days) | Ret. Time (min.) | Area (main peak) × 10 | Total Area × 10 | Fraction Main Peak |
|---|---|---|---|---|
| 0 | 20.95 | 2.84 | 2.84 | .998 |
| 0 | 19.85 | 2.96 | 2.98 | .995 |
| 0 | 20.88 | 2.89 | 2.94 | .985 |
| avg. | 20.6 ± 0.6 | 2.90 ± .06 | 2.92 ± .07 | .993 ± .007 |
| 14 | 19.78 | 2.68 | 2.75 | .977 |
| 14 | 19.72 | 2.51 | 2.52 | .997 |
| avg. | 19.8 ± .03 | 2.60 ± .09 | 2.64 ± .01 | .987 ± .01 |
| 30 | 20.2 | 2.57 | 2.68 | .959 |
| 30 | 21.8 | 2.36 | 2.47 | .955 |
| avg. | 21.0 ± .8 | 2.47 ± .1 | 2.58 ± .1 | .957 ± .002 |
| 97 | 20.2 | 2.62 | 2.69 | .974 |
| 97 | 20.2 | 2.57 | 2.61 | .984 |
| avg. | 20.2 | 2.60 ± .03 | 2.65 ± .04 | .979 ± .005 |
| 150 | 20.7 | 2.84 | 2.98 | .957 |
| 150 | 20.7 | 2.81 | 2.92 | .961 |
| 150 | 20.7 | 2.82 | 2.96 | .955 |
| avg. | 20.7 | 2.82 ± .02 | 2.95 ± .03 | .958 ± .003 |

First Order Rate Constants for Degradation of Main RP-HPLC Peak of Human Relaxin after one year at 5° C. Data at each time point were averaged in triplicate (when available) and used to fit: In (fraction main peak) = A − kt

| intercept | k(days− ) | R | t.9 | t1/2(yr) |
|---|---|---|---|---|
| −0.027 ± 0.007 | −0.00008 ± 0.00004 | .746 | >2 yrs | >2 |

TABLE IV

REVERSE PHASE HPLC STABILITY OF CITRATE FORMULATION STORED AT −20° C.

| Time (days) | Ret. Time (min.) | Area (main peak) × 10 | Total Area × 10 | Fraction Main Peak |
|---|---|---|---|---|
| 0 | 19.70 | 4.25 | 4.29 | .990 |
| 0 | 19.70 | 4.22 | 4.24 | .995 |
| 0 | 19.72 | 4.19 | 4.21 | .993 |
| avg. | 19.71 ± .01 | 4.22 ± .03 | 4.25 ± .04 | .993 ± .003 |
| 30 | 20.22 | 4.31 | 4.35 | .989 |
| 30 | 20.20 | 4.29 | 4.32 | .994 |
| avg. | 20.21 ± .01 | 4.30 ± .01 | 4.34 ± .02 | .989 ± .005 |
| 60 | 19.82 | 4.76 | 4.86 | .979 |
| 60 | 19.87 | 4.61 | 4.67 | .991 |
| 60 | 19.85 | 4.59 | 4.63 | .992 |
| avg. | 19.85 ± .03 | 4.65 ± .09 | 4.72 ± .12 | .987 ± .007 |

Stability of relaxin in terms of its bioactivity was followed by using an assay that measures the production of cyclic AMP mediated by the interaction of relaxin with rhesus monkey uterine cells. The cyclic AMP bioassay plots of concentration versus time are shown in FIGS. 3a–3e, where FIG. 3a is relaxin in glycine-HCl (pH 3.0), FIG. 3b is relaxin in citrate (pH 5.0), FIG. 3c is relaxin in acetate (pH 5.0), FIG. 3d is relaxin in histidine (pH 6.0), and FIG. 3e is relaxin in Tris buffer (pH 7.5). In all figures, the open squares are 5° C., the solid circles 25° C., and the open triangles 40° C., and the straight line is expected value. Within the errors of the experiment it appears that all samples (pH from 3 to 7.5) had equivalent bioactivity after 40-days storage.

Stability of relaxin regarding its bioactivity was also assessed using the mouse pubic symphysis assay. A comparison of bioactivity for undegraded relaxin in citrate buffer at pH 5 to a highly degraded sample in Tris buffer at pH 7.5 revealed that within the errors of the assay there were no differences in bioactivity.

An ELISA and a circular dichroism assay were used to assess protein conformation of the formulations. The data demonstrate that the tertiary structure of the relaxin is unaltered after 1 or 2 months of storage.

Potential alteration in protein self-association was investigated using the sedimentation equilibrium analytical ultracentrifugation technique. Relaxin in 10 mM acetate, 0.1M NaCl at pH 5 was analyzed by analytical ultracentrifugation at loading concentrations of 0.1, 0.2, and 0.4 mg/ml. The weight average molecular weight at all three loading concentrations is about 10,000, demonstrating that relaxin under these conditions forms dimers.

Figure 4:
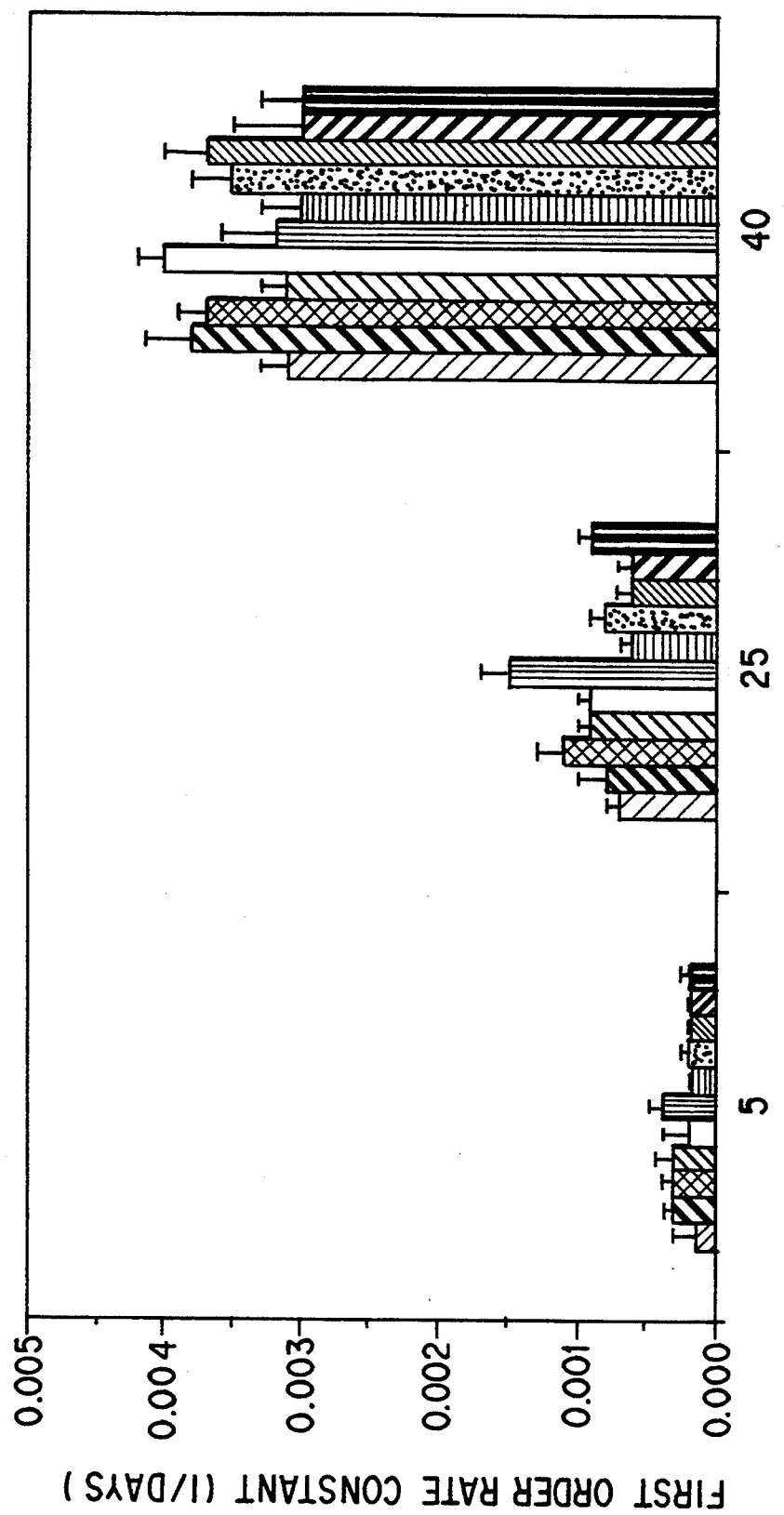
FIG. 4 represents a bar graph of the rate of degradation at 25° C. of the main reverse phase HPLC peak in a citrate formulation of pH 5 having different stabilizing agents added thereto.

Various pharmaceutically acceptable excipients were added to the 10 mM citrate, pH 5 formulation to investigate their effect on the stability of the formulation. FIG. 4 is a graph showing the rate of degradation of the main reverse phase HPLC relaxin peak for the various formulations at the three temperatures. From left to right, ultrafiltered (solid) and dialyzed (dense hatching) samples were compared to samples with excipients added as follows: an isotonic amount (cross hatching) or 5% (medium hatching) by weight of mannitol, 5% (open) or 10% (solid) by weight of glycerol, 5% (horizontal) or 10% (dotted) by weight of ethanol, 5% (light hatching) or 10% (open) by weight of propylene glycol, and 0.02% (solid) by weight of EDTA. Each was stored at 5, 25, or 40° C. As can be seen, the excipients had a negligible effect on stability as compared with the ultrafiltered and dialyzed controls, within experimental error. The dialyzed and ultrafiltered samples also showed no differences between each other within experimental error.

In addition, lyophilized formulations may be prepared wherein the relaxin would be reconstituted as an acidic solution. More specifically, long relaxin was dialized into 10 mM citrate, 0.507% mannitol, pH 5.0, after initially being present in the citrate formulation buffer. This preparation was then sterile-filtered into nine 3cc vials at a volume of 1 ml. each. These vials were placed on a tray in a Lyovac GT 20 lyophilizer. The relaxin samples were cooled to −50° C. and then subjected to a primary drying cycle of 25 hours at 0° C. This was followed by a secondary drying cycle of 17.5 hours at 25° C. At the termination of the lyophilization, one vial was reconstituted with one ml. of Milli-Q water, and appeared quite clear, free of turbidity, indicating a successful reconstitution. Thus, the remaining vials were placed on stability at 5° C. and 25° C.

Long relaxin that was exchanged into the lyophilization buffer prior to lyophilization was used as a pre-lyophilization control. In addition to the time-zero reconstituted sample, samples were reconstituted after 2 weeks, one month, and 3 months of storage at both 5° C. and 25° C. All samples were analyzed for degradation products by RP-HPLC as previously described. The average of triplicate injections was made whenever possible. The % main peak was unchanged (see Table IVa) for all samples regardless of the length of time stored lyophilized, indicating no loss of stability after 3 months at 25° C. In addition, spectrophotometric analysis of all samples indicated no increase in the % light scattering subject to up to 3 months storage lyophilized at 25° C.

TABLE IVa

| Sample | % Main Peak |
| --- | --- |
| pre lyophilization control: | 97.3% |
| time zero reconstitution: | 97.8 ± 0.7% |
| 2 weeks, 5° C. | 98.3 ± 0.3% |
| 2 weeks, 25° C.: | 98.1 ± 0.4% |
| 1 month, 5° C.: | 97.8% |
| 1 month, 25° C.: | 97.6% |
| 3 months, 5° C.: | 98.0 ± 0.5% |

TABLE IVa-continued

| Sample | % Main Peak |
| --- | --- |
| 3 months, 25° C.: | 98.8 ± 0.4% |

Preliminary freeze-thaw studies indicate that the protein can be frozen in a liquid formulation at −20° and −60° C. at a concentration of 2 mg/ml at pH 5 without any observed changes in the HPLC assay. In addition, Table V provides the RP-HPLC stability data for the citrate, pH 5.0, formulation frozen, then thawed, with a sample taken, then frozen immediately and kept frozen for 30 days, then thawed for 5 hours at room temperature. No change in the HPLC data was observed upon thawing.

TABLE V

REVERSE PHASE HPLC (FREEZE-THAW) STABILITY OF CITRATE FORMULATION STORED AT −20° C.

| Time (days) | Ret. Time (min.) | Area (main peak) × 10 | Total Area × 10 | Fraction Main Peak |
| --- | --- | --- | --- | --- |
| ZERO TIME SAMPLE REFROZEN | | | | |
| 30 | 20.18 | 4.50 | 4.54 | .989 |
| 30 | 20.18 | 4.51 | 4.56 | .989 |
| 30 | 20.20 | 4.48 | 4.53 | .987 |
| avg. | 20.19 ± .01 | 4.50 ± .02 | 4.54 ± .02 | .988 ± .001 |
| 5 HOURS AT ROOM TEMPERATURE* | | | | |
| 0 | 19.82 | 4.76 | 4.86 | .979 |
| 0 | 19.87 | 4.61 | 4.67 | .991 |
| 0 | 19.85 | 4.59 | 4.63 | .992 |
| avg. | 19.85 ± .03 | 4.65 ± .09 | 4.72 ± .12 | .987 ± .007 |
| 5 hrs | 19.88 | 4.60 | 4.65 | .989 |

*: 60 day sample in frozen state at −20° C. was stored for 5 hours at room temperature and reassayed.

In conclusion, the structural integrity of human relaxin as measured by RP-HPLC is affected by the pH at which it is formulated, and degradation occurs at pH 7 and higher. The HPLC assay reveals that of the five formulations investigated, relaxin is more stable in an acetate or citrate buffer at pH 5 than in other buffers, and the citrate buffer at pH 5 is the most stable at 5° and −20° C. for up to five months. Bioactivity is not affected.

EXAMPLE II

In a comparison of porcine and human H2 relaxin, weight average molecular weight data showed that human relaxin associates in solution at pH 5 to a far greater extent than does porcine relaxin. The data for human relaxin obtained at different loading concentrations were similar, suggesting that the aggregation is a reversible self-association. The data also show that the self-association for human relaxin is less extensive at pH 3 than at pH 5.

EXAMPLE III

It has been found that the natural form of relaxin is one that has a B chain with 29 amino acids (short relaxin) rather than 33 amino acids (long relaxin). The purpose of this study was to determine if the short relaxin has similar stability and adsorption characteristics when compared with the long form. In addition, the two forms of relaxin were compared for their UV extinction coefficients at 280 nm and secondary structure using far UV CD.

The short relaxin employed in these experiments was obtained by limited proteolysis of the long relaxin (synthesized in Example I) so as to obtain 29 amino acids in the B chain. After synthesis of the long relaxin, it was applied to an HPLC column using a TFA gradient and then mono S ion exchange column. The relaxin-containing fragments were then diafiltered into a formulation buffer. To the buffer (containing 200 mg relaxin) was added 1 part trypsin to 2000 parts by weight relaxin and the proteolysis carried out for about 40 minutes. Then 50 μl of a 16.9 mg/ml solution of carboxypeptidase B (70 u/mg) was added to the digest. The resulting solution was left for 1 hour at room temperature, then acidified using citric acid, and purified by HPLC and monoS columns. The relaxin so purified was diafiltered into 10 mM citrate isotonic with sodium chloride pH 5 at 1.0 mg/ml and stored frozen at −60° C. (1 ml in 3-cc type I glass vials). A portion of this lot was also supplied as liquid and designated as a non-frozen sample.

Temperature Stability: The stability of relaxin in 10 mM isotonic citrate at pH 5 was assessed by following the first order rate kinetics of reduction of the main reverse phase HPLC peak. Chromatograms were obtained on a SynChropak ™ C4 reverse phase column using the following conditions: 1 ml/min. flow rate, gradient of 20% Solution A to 50% Solution B over thirty minutes (Solution A is 0.1% trifluoroacetic acid and Solution B is 0.1% trifluoroacetic acid, 90% acetonitrile).

Table VI shows a comparison of the kinetics between long relaxin and short relaxin. The first-order rate constants for long relaxin were determined from one-year stability data and those of the short form from 6-month data for frozen-thawed samples and 2-month data for non-frozen samples. Included with the determined first-order rate constants are values for t0.9 and t½. The stability of the short form is at least as good as that of the long relaxin, and may be better since there is a greater than 2-year stability at 25° C. for the frozen-thawed sample. As observed previously for long relaxin, freezing and thawing does not affect the stability of the short relaxin.

TABLE VI

First Order Rate Constants for Degradation of Main RP-HPLC Peak of Long and Short Relaxin
Average of triplicates were used to fit:
ln(fraction main peak) = A − kt

| Buffer | Intercept | k(days$^{-1}$) | t.9 (days) | t1/2 (days) |
|---|---|---|---|---|
| *Long Form* | | | | |
| 5° C. | −0.027 ± 0.007 | −0.000082 ± 0.000037 | >2 yrs | >2 yrs |
| 25° C. | −0.028 ± 0.010 | −0.000591 ± 0.000055 | 178.2 | >2 yrs |
| 40° C. | −0.028 ± 0.024 | −0.002603 ± 0.000132 | 40.5 | 266.3 |
| *Short Form (Non-Frozen)* | | | | |
| 5° C. | −0.007 ± 0.005 | −0.000116 ± 0.000132 | >2 yrs | >2 yrs |
| 25° C. | +0.002 ± 0.004 | −0.000516 ± 0.000106 | 204.1 | >2 yrs |
| 40° C. | −0.001 ± 0.008 | −0.003988 ± 0.000194 | 26.4 | 173.8 |
| *Short Form (Frozen-Thawed)* | | | | |
| 5° C. | −0.005 ± 0.003 | −0.000037 ± 0.000032 | >2 yrs | >2 yrs |
| 25° C. | −0.005 ± 0.006 | −0.000478 ± 0.000220 | >2 yrs | >2 yrs |
| 40° C. | −0.001 ± 0.007 | −0.002773 ± 0.000247 | 52.4 | 345.0 |

Light Stability: Two vials of short relaxin were placed in a light box with a rating of 1600 foot candles for seven days. One of the vials was shielded from the light with aluminum foil and served as a control. The retention times (R$_t$) of the main relaxin peaks of long relaxin were normalized to that of the short form and are shown in Table VII. All retention times of the degradation peaks were then related to this normalized value. As can be seen, the normalized retention times for both short and long relaxin are in excellent agreement, suggesting that similar pathways of degradation are occurring in both proteins. However, the rate of degradation of the long relaxin appears to be somewhat greater than that of the short relaxin.

TABLE VII

Light Stability of Short and Long Relaxin

| Long Form | | Short Form | |
|---|---|---|---|
| R$_t$# | % Remaining Main Peak* | R$_t$# | % Remaining Main Peak* |
| *7 days exposure to 1600 foot-candles of light* | | | |
| 19.34 ± 0.01 | 64.07 ± 0.53 | 19.34 ± 0.01 | 78.56 ± 0.64 |
| 17.62 ± 0.08 | 7.38 ± 0.20 | 17.67 ± 0.02 | 8.56 ± 0.16 |
| 17.20 ± 0.08 | 11.26 ± 0.19 | 17.38 ± 0.01 | 4.90 ± 0.022 |
| 15.49 ± 0.03 | 4.68 ± 0.13 | | |
| *Control* | | | |
| 19.33 ± 0.02 | 97.16 ± 0.37 | 19.33 ± 0.02 | 97.09 ± 0.26 |
| 19.13 ± 0.02 | 1.88 ± 0.15 | 19.02 ± 0.02 | 2.03 ± 0.16 |

Retention times of the main peak are normalized to that of the short form and those of the degradation peaks are related to the normalized value.
*Peaks with areas less than 2% of total area were omitted for clarity.

Stability to Agitation: A vial of short relaxin was agitated at room temperature for seven days on a Glas-Col model S-500 agitator at a setting of 2.5 units. A control vial was kept undisturbed at room temperature. The stability of the relaxin was assayed by reverse-phase HPLC as described above for the temperature stability assay.

Table VIII shows the percent of the main relaxin peak remaining after seven days of agitation. These data indicate that there was no significant change detected by reverse phase HPLC in the agitated sample when compared to the non-agitated control, in either the long or short relaxin.

TABLE VIII

Stability To Agitation of Short and Long Relaxin

| Long Form | | Short Form | |
|---|---|---|---|
| Rt | % remaining main peak | Rt | % remaining main peak |
| *Control* | | | |
| 19.97 ± 0.02 | 97.84 ± 0.17 | 19.26 ± 0.04 | 98.50 ± 0.28 |
| *Agitated* | | | |
| 19.97 ± 0.02 | 98.53 ± 0.43 | 19.17 ± 0.03 | 98.45 ± 0.23 |

Adsorption Study: The relaxin was diluted to about 10 μg/ml determined by UV spectrophotometry in normal saline. Two feet of Silastic$^R$ tubing 0.02 in. internal diameter × 0.037 in. outer diameter was connected to a Harvard infusion pump equipped with a 5-ml glass syringe and a 22 G needle. Relaxin was infused at 100 μl/min. through the tubing with a 100-μl sample collected every minute for the first ten minutes, followed by a 100-μl sample every five minutes to thirty minutes, into 900 μl of the ELISA assay buffer (EAB). This 1:10 dilution was diluted to 1:4000 by two subsequent dilutions in EAB. The 1:4000 dilution was submitted to a protein concentration determination by ELISA.

The relaxin adsorbed onto the tubing. However, after five minutes of infusion through the tubing, the relaxin concentration was close to the expected concentration of 10 ng/ml as determined by the ELISA. Integration of the area under the curves showed a loss of about 5% of the total mass of protein due to adsorption onto the surface of the tubing. There does not appear to be a significant difference in the adsorption to the Silastic$^R$ tubing between the two forms of relaxin.

Determination of Extinction Coefficient: The extinction coefficients for long and short relaxins were calculated by quantitative amino acid analysis from two separate determinations to be 2.04 or 2.14 cm$^2$/mg for long relaxin and 2.25 or 2.30 cm$^2$/mg for short relaxin. The molar extinction coefficients calculated for long and short relaxin were 13,000±200 M$^{-1}$cm$^{-1}$. This result suggests that the removal of the four amino acids from the C-terminus has little effect on the immediate environment of the two tryptophans and one tyrosine. This also suggests that the conformations of the two forms of relaxin are similar.

Circular Dichroism: The circular dichroism spectra from 240 to 190 run of long relaxin (at 0.8 mg/ml) and short relaxin (at 1 mg/ml) in 10 mM isotonic citrate at pH5 were determined with an Aviv Cary 60 spectropolarimeter. The samples were thermostated in 0.01 cm path length cylindrical quartz cuvettes. The CD output in millidegrees was converted to mean residue weight ellipticity using a mean residue weight of 113 and relaxin concentrations that were obtained using UV absorption at 278.4 nm. The concentration of relaxin was determined using extinction coefficients of 2.04 and 2.25 cm$^2$/mg for long and short relaxin, respectively. Estimates of secondary structure were determined by the method of Chang et al., *Anal. Biochem.*, 91: 13–31 (1978).

Analysis of the far UV CD spectra by the method of Chang et al., supra, resulted in 50% alpha helix, 47% beta sheet, and 3% random coil for the long relaxin, and 50% alpha helix and 50% beta sheet for the short relaxin. The differences in the spectra for short and long relaxin are Well within experimental error and strongly suggest that the secondary structure of short and long relaxin is very similar.

Conclusion: The thermal stability of the short relaxin is comparable to and perhaps exceeds that of the long relaxin in the liquid formulation. Furthermore, stability to light exposure and agitation are also similar in the two proteins. Physical properties such as molar extinction, secondary structure, and adsorption to surfaces also appear identical.

EXAMPLE IV

This example illustrates the preparation and properties of relaxin gel formulations.

Liquid Relaxin Preparation

The short relaxin (with the 29-amino acid B-chain) prepared and formulated as described in Example III was used for this experiment. Thus, the relaxin was in a concentration of 1.0 mg/ml, 1 ml in 10 mM citrate, isotonic with NaCl, pH 5.0. This formulation was stored frozen in vials at −60° C. until just prior to use. Relaxin from these vials was concentrated to greater than 2.4 mg/ml (as determined by UV spectroscopy, assuming e=2.04 ml/mg.cm) by centrifugation at 4000 rpm for one to two hours in a 2-ml Amicon Centricon 10 microconcentrator. (The exact time is dependent on the initial volume of relaxin needed to be concentrated.)

4% Methocel Gel Preparation

A 4% methylcellulose gel was reconstituted from Methocel A 4M methylcellulose powder (Dow Chemical) according to the following protocol:

(a) 10 ml of citrate formulation buffer (described in Example I) was heated to near boiling (~90° C.) in a 40-ml beaker with a stir bar present, and then removed from the heat.

(b) 0.8 g of Methocel powder was added to the beaker, swirling for a few seconds to disperse the particles.

(c) The beaker was then placed on a magnetic stirrer in the cold room at 5° C. Immediately, before the liquid started to thicken, an additional 10 ml of cold citrate formulation buffer was added, flushing any dry particles from the sides of the beaker.

(d) After 20 minutes of continuous stirring, the viscosity of the liquid increased until a homogeneous 4% methylcellulose gel was formed.

(e) For the last two stability studies, the 4% methylcellulose gel was autoclaved, not only to sterilize the gel, but also to remove any dissolved oxygen present within the gel. After removal from the autoclave, the gel was stirred under a nitrogen head space to rehomogenize the gel without introducing any new oxygen.

Preparation of Topical Relaxin

A homogeneous 3% Methocel gel of 600 μg/ml relaxin was obtained following the protocol below:

(a) Two sterile 10-cc syringes were tared on the balance. To one syringe was added 3 g of the 4% Methocel gel. To the other syringe was added the 2.4 mg/ml liquid relaxin formulation at one third the volume of the gel (1 ml).

(b) The plungers were returned to the two syringes, and the two syringes were connected by a sterile Rainin 47-FLU connector, which screws onto the ends of the two syringes.

(c) The relaxin solution is dispersed into the methylcellulose by pushing in one syringe plunger, followed by the other syringe plunger, 20–25 times, at which point a homogeneous gel is formed. (However, in the last two experiments, the gel was then transferred to 1.5-ml eppendorf tubes for ease of storage and sample removal.) The final concentration of relaxin in the gel was 600 μg/ml. The gel also contained 3% methylcellulose, 10 mM citrate, pH 5.0, and isotonic with sodium chloride.

ELISA Assay

Samples of relaxin in the gel were diluted with the same ELISA diluent as used in Example I in sequential ten-fold steps to arrive at a concentration of 6 ng/ml relaxin. There appeared to be no effect of up to 0.25% Methocel Gel upon the relaxin concentration as determined by ELISA. The ELISA assay, described above, revealed that relaxin concentrations in the gel were 25% lower than those expected, based on UV spectroscopy (assuming an extinction coefficient of 2.04). This result is due to the assay standard being full-length B-chain relaxin and the samples submitted being shortened B-chain relaxin.

RP-HPLC Analysis of Topical Relaxin

The RP-HPLC method used for analyzing the liquid relaxin formulation, described in Example I, was modified for use with topical relaxin samples. Due to the high viscosity of the gel, samples were diluted ten-fold with water, vortexed for ~5 minutes to homogenize the gel, and left undisturbed to let the bubbles rise. Analysis of these samples was performed by injecting 250 μl onto a C4-300 SynChropak (4.6×250 mm) column at room temperature. The initial equilibration buffer was 18% acetonitrile, 0.1% trifluoroacetic acid. The elution was carried out by running a 1%/min. increasing linear acetonitrile gradient to a final concentration of 45% acetonitrile after 30 minutes. The flow rate was held constant at 1.0 ml/min. and the absorbance was monitored at 214 nm. The "slowdown" step (the time it takes to draw the viscous gel into the metering device) was increased from 36 to 270 minutes. It was found that prior to increasing the "slowdown" step, significantly less than 250 μl of gel was actually being injected due to its high viscosity.

During the course of these experiments, the SynChropak column began to lose its ability to resolve peaks. Thus, the last few injections were done on a C4-300 Vydac column.

Three significant stability experiments were performed on the topical relaxin formulation. The first was to measure the stability of these preparations after being left out at room temperature for five weeks. The sample remained in the original syringe, subject to the fluctuations of temperature and light.

RP-HPLC analysis revealed that the main, undegraded relaxin peak was subject to increasing amounts of degradation with time as evidenced by the decrease in the % area of the main peak and an increase in the number and % area of the earlier-eluting degradation peaks. The decrease in the % area of the main peak was quantitated and normalized with respect to the % main peak at time zero (prior to putting the relaxin into the gel). A log plot of the normalized fraction main peak versus time revealed that the topical relaxin had undergone first-order degradation kinetics.

Both the main relaxin peak and the largest degradation peak were collected from the HPLC effluent and lyophilized under vacuum in the Savant Speed-vac for ~1 hour. These samples were then reconstituted in thioglycerol and acetic acid, reduced on the probe to separate the A and B chains, and analyzed by mass spectrometry. The mass spectrometry analysis of these two samples revealed that the molecular ion for the A-chain of both samples was identical, and agreed with the predicted value of ~2657. However, the molecular ions of the B-chains were different. The molecular ion for the main peak sample agreed with the theoretical value of ~3314. The molecular ion for the B-chain from the degraded peak was ~3330. This increase of 16 corresponds exactly to what would be expected if a residue in the B-chain had become oxidized.

Porcine relaxin from pig ovaries, at 6.6 mg., was reconstituted into citrate formulation buffer, spun down for ~3 minutes to pellet any particulates, and mixed at 3.19 mg/ml in 0.248 ml citrate formulation buffer with 4% Methocel as described above to yield a 3% gel with 600 μg/ml porcine relaxin. In contrast to the shortened B-chain human relaxin, the porcine relaxin formulation degraded very little when subjected to HPLC analysis as described above.

The second study was a measure of the stability of topical relaxin under well controlled conditions at 5° C. and 25° C. In addition, the Methocel Gel for this study was autoclaved to sterilize it and remove any dissolved oxygen from the gel that might cause oxidation. Samples of the topical relaxin were transferred to four eppendorf tubes, two stored at 5° C. and two stored at 25° C. After 144 hours, the topical relaxin at 5° C. started to degrade, while the material at 25° C. was relatively undegraded, as determined by HPLC analysis. Subsequent analysis revealed that the lights in the 5° C. cold room were often left on, while the 25° C. box was completely shielded from all light sources.

To determine if this light was responsible for the formation of the degradation peaks at 5° C., one of the two samples was wrapped in aluminum foil to shield it from the light. After an additional 360 hours at 5° C., the exposed relaxin had completely degraded while the shielded relaxin had continued to degrade at a much slower rate, as determined by HPLC. Thus, the presence of light appeared to affect the stability, with shielding from light completely protecting the topical relaxin, but exposure to light and covering causing continued degradation at a much slower rate. Mass spectrometry of the collections of the broad peaks in the topical relaxin stored for 672 hours (both covered and exposed to light) revealed that the A-chain was unaffected, but the B-chain appeared to undergo a first, then a second, oxidation.

The third experiment was to compare directly the stability of the topical relaxin to that of the liquid-formulated relaxin, both exposed to and shielded from light. After 816 hours stored at 5° C., RP-HPLC chromatograms indicated that when shielded from light, the topical relaxin was just as stable as the liquid-formulated relaxin, with both having 96% main peak. However, when exposed to light, the topical relaxin was dramatically more susceptible to degradation than the liquid-formulated relaxin.

Efficacy Studies

The purpose of this study is to determine the efficacy of short relaxin on the ripening of the rabbit cervix. The rabbit was chosen because studies have suggested that this animal is a reasonably good model for the investigation of the mechanical behavior of the cervix and because the rabbit cervix appears to be comparable to the human cervix in its physiologic responses.

Mature pregnant female New Zealand rabbits weighing 4.5 to 6.0 kg were studied. On day 26-27 of pregnancy, the rabbits (4 per group) were treated with either the short human relaxin gel or porcine relaxin gel prepared as described above in a 3% methylcellulose gel. Both short human relaxin and porcine relaxin were formulated at doses of 100, 200, 300, 600, and 1000 μg/ml relaxin per animal. Both hormones were applied intravaginally by means of a syringe and a catheter in a volume of 0.5 ml. Control animals received the vehicle alone. After 16–18 hours, the animals were sacrificed using a lethal dose of pentobarbital. The uterus, the lower segment, and the cervix were removed and fixed for histologic examination in 10% NB Formalin. Paraffin sections were cut and stained with hematoxylin-/eosin and alcian blue PAS. Sections were evaluated for general morphology, and specifically for the degree of separation of muscular tissue and collagen fibrils in the submucosa and for the presence of characteristic PAS positive giant cells, which are multinucleate cells of macrophage origin that normally infiltrate the cervix during labor. The measurement of giant cells is accomplished using the procedure described by MacLennan et al., *Am J. Obstet. Gynecol.*, 152:691–696 (1985).

An initial study in which a concentration of 300 μg/ml of human or porcine relaxin was employed in a topical formulation suggested that at this dose both hormones induce changes in the morphology of the pregnant cervix consistent with ripening. Eighteen hours after application to the cervix, significant dilation and cervical ripening were observed. Histological evaluation of stained cervix sections showed marked separation of the muscularis mucosa with accumulation of slightly protein-rich material in the intervening spaces, separation of the collagen fiber bundles (a decrease in collagen density), increase in the ground substance, and submucosal edema with dilatation of the lymphatic vessels. Also, Characteristic PAS positive giant cells, which are rare in the control animals, were abundant in the relaxin-treated groups. Such cells were seen most commonly around the blood vessels and in the subepithelial layer, although they could be found throughout the depth of the cervix. Subsequent studies in which it was attempted to define the lowest and, if possible, the maximal efficacious dose of relaxin were contrary to the earlier results, with no efficacy seen at 300 or 600 μg/ml, and efficacy clearly seen only with the dose of 1 mg/ml.

Pharmacokinetic Studies

The objective of this study was to determine the bioavailability of short relaxin in pregnant rabbits after single intravenous, subcutaneous, and intravaginal administrations.

The rabbits employed were 16 timed pregnant multiparous female New Zealand white rabbits (Elkhorn), 4–5 kg. At day 26 of gestation, four animals (Group I) received 100 μg/kg short relaxin by intravenous bolus (iv) through an Abbocath-T catheter in an ear vein. Three animals (Group II) received a 100 μ/kg subcutaneous (sc) dose of short relaxin in sterile saline in the thigh. Three animals (Group 5) received a 100 μg/kg sc dose of short relaxin in 1% benzopurpurine. Four animals (Group 3) received a 100 μg/kg intravaginal dose of short relaxin in 3-methylcellulose. The dose solution concentration iv and sc was 500 μg/ml of a clear short relaxin liquid at 1 mg/ml relaxin. Dilutions were made with sterile isotonic saline or 1% benzopurpurine (BPP) in saline. The dose volume was approximately 1 ml and was calculated individually according to the following equation:

Dose volume=(100 μg/kg)(kg)/(500 μg/ml).

For intravaginal administration, a total of 3 mg of Methocel gel (4%) was mixed with 0.487 ml of short relaxin (described above) and 0.513 ml of citrate formulation buffer following the protocol described above, to yield a 600 μg/ml short relaxin, 3% methylcellulose gel. The intravaginal dose volume was 0.5 ml.

Blood samples (1 ml) were drawn from a Viggo Secalon catheter in the artery of the ear. Blood sampling times were: (iv) 0, 1, 2, 3, 4, 5, 7, 10, 20, 40, 60, 80, 120, 180, 240, 300, 360, 420, 480, 540, 600, 660, and 720 min.; (sc and intravaginal) 0, 1, 2, 3, 5, 7, 10, 15, 20, 30, 40, 50, 60, 75, 90, 120, 180, 240, 300, 360, 420, 480, 540, 600, 660, and 720 min. Blood samples were allowed to clot and serum was harvested by centrifugation. Samples were frozen on dry ice and stored at −70° C. until assayed by ELISA. The assay range was 20 to 1280 pg/ml.

Individual iv pharmacokinetic parameters were estimated by fitting the individual immunoreactive serum concentration-time data to a three-exponential model using a nonlinear curve fitting program (NONLIN84, Statistical Consultants, Inc.; Lexington, Ky.). Data from extravascular routes of administration were fitted using the RS-1 program (Bolt, Bernak & Newman, Cambridge, MA). The area under the serum concentration-time curve (AUC) was computed using the trapezoidal method from t+0 to the last measurable serum concentration (Ct). The AUC from Ct to infinite time was estimated by extrapolation: Ct was divided by the terminal elimination rate constant. Serum clearance (CL) was calculated by the equation: CL=Dose/AUC(iv). The initial volume of distribution (Vc) was calculated from: Vc=Dose/C(0), where C(0) was the sum of the coefficients of the tri-exponential equation describing the serum concentration-time data. The volume of distribution at steady-state (Vdss) was calculated as: CL*AUMC/AUC, where AUMC was the area under the moment curve, i.e., the (serum concentration)*(time) vs. time curve. Serum half-lives were calculated by dividing 0.693 by the respective disposition rate constant. Bioavailability was determined by the areas ratio method: (AUC (extravascular)/AUC(iv))* 100.

Figure 5:
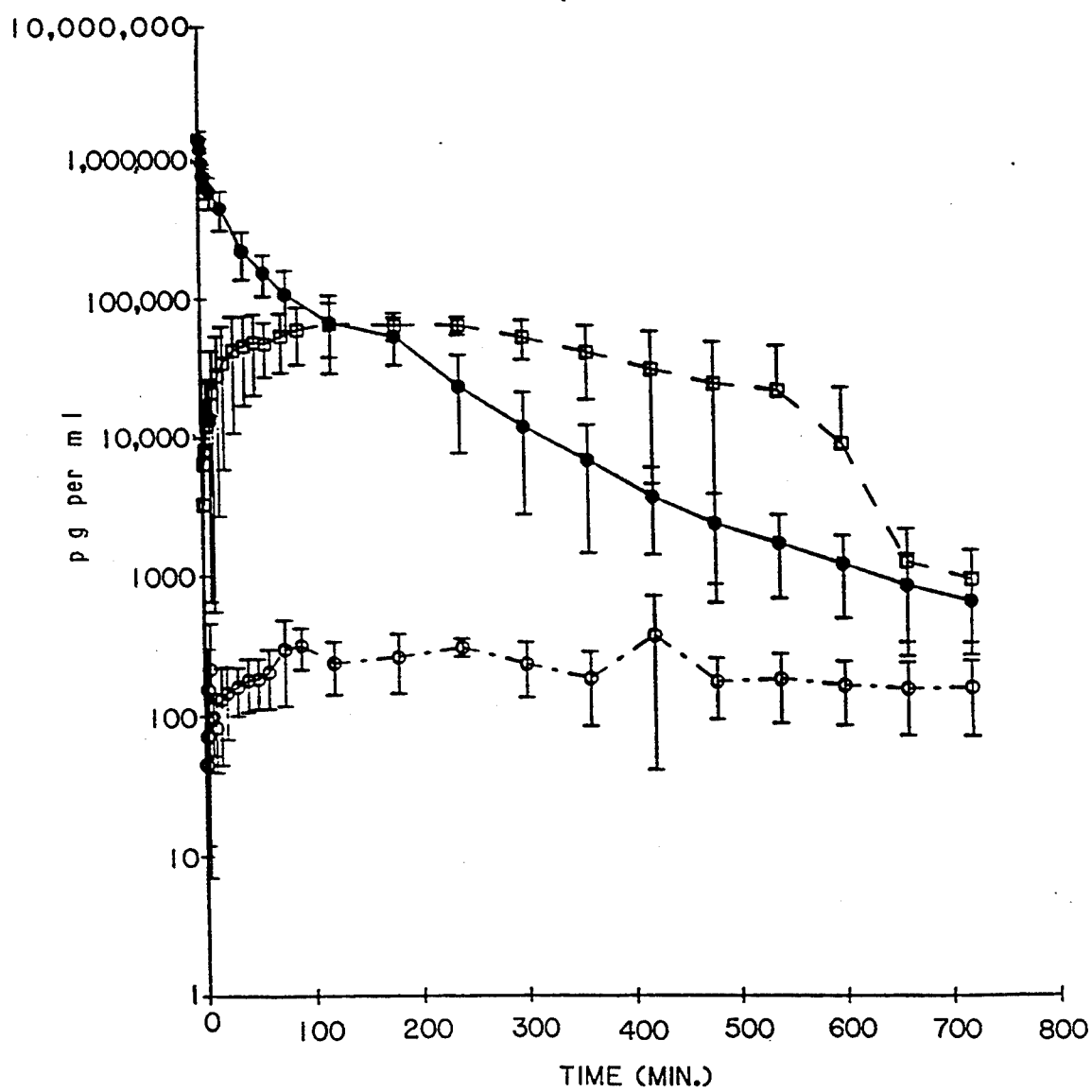
FIG. 5 represents a graph of serum concentration versus time for short relaxin in pregnant rabbits after intravenous, subcutaneous, and intravaginal administration.
Figure 6:
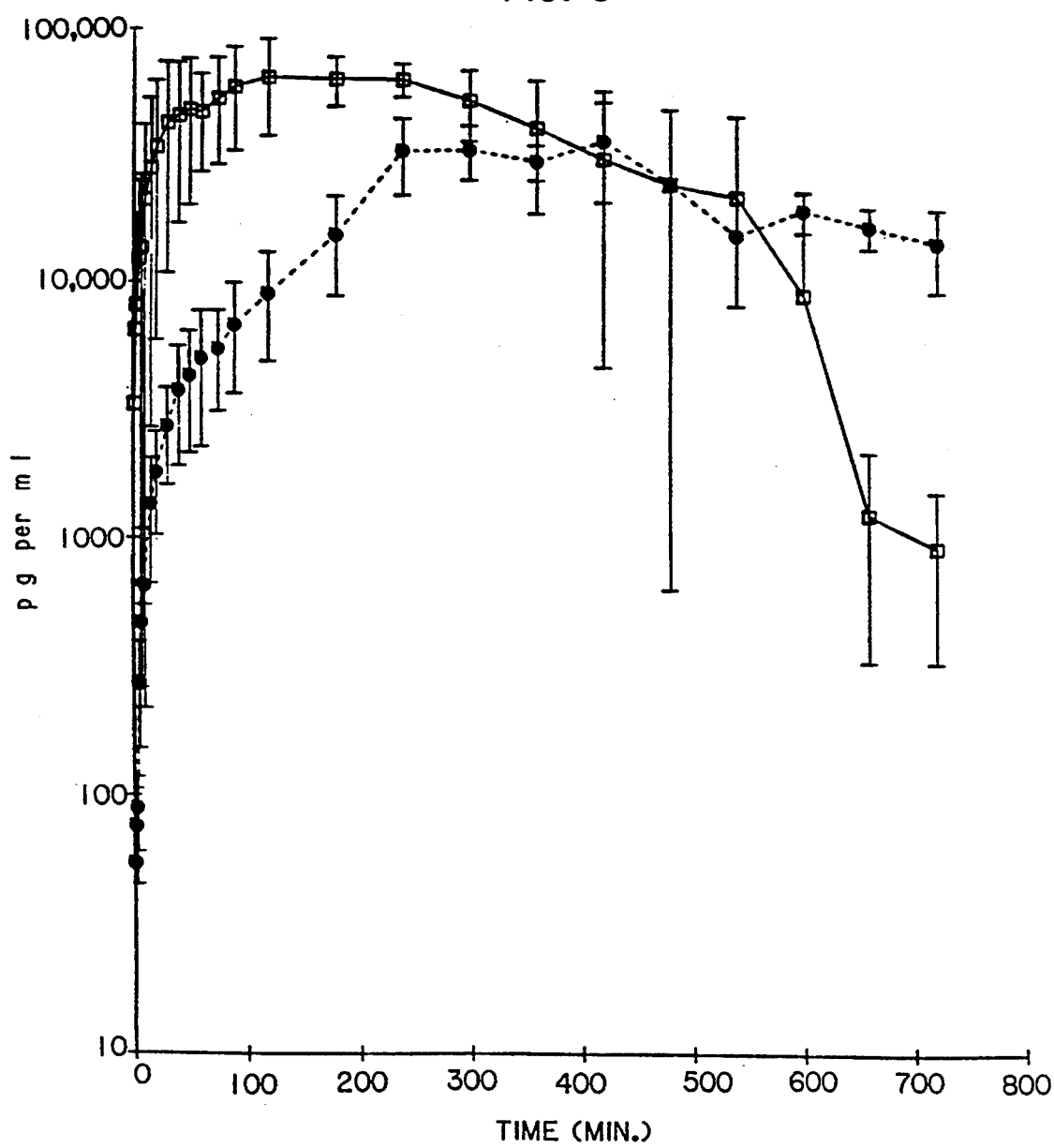
FIG. 6 represents a graph of serum concentration versus time for short relaxin in pregnant rabbits after subcutaneous administration with and without benzopurpurine.

The serum concentration-time profiles for 100 μg/kg short relaxin in pregnant rabbits after iv, sc, and intravaginal administration are shown in FIG. 5, where the closed circles are iv, the open squares are sc, and the open circles are intravaginal administration.. FIG. 6 shows a comparison of the serum concentration-time profiles for 100 μg/kg short relaxin, administered subcutaneously to pregnant rabbits with (closed circles) and without (open squares) BPP. Table X lists the calculated pharmacokinetic parameters for all routes of administration. The serum clearance (CL) after iv administration was 2.95±0.88 ml/min./kg. The initial (Vc) and steady state (Vdss) volumes of distribution were 89±22 and 209±30 mg/kg, respectively. Three exponential terms were required to describe the iv serum concentration-time data, so that the half-lives (t½) were 8.4±2.7, 59.1±8.7, and 279±128 min., respectively. Subcutaneous administration of human relaxin resulted in a mean peak serum concentration of 76.20±17.80 ng/ml at 180 min. and a bioavailability of 76.0±20.6% (with iv relaxin having 100% bioavailability). Human relaxin administered sc with BPP yielded a mean peak serum concentration that was lower (41.67±16.32 ng/ml) and later (420 min.) than that observed with human relaxin administered sc alone. The sc bioavailability with BPP was 59.4±6.7%.

Human relaxin appeared to be poorly absorbed systemically after intravaginal administration. Systemic serum concentrations were very low (0.34±0.16 ng/ml at 98 min.) and the resultant bioavailability was only 1.0±0.8%.

TABLE X

Pharmacokinetic parameters for 100 μg/kg hRlx in pregnant rabbits after iv, sc and intravaginal administration.

| Route | 1) AUC (ng − min/ml) | 2) CL (ml/ min/kg) | 3) Vc (ml/kg) | 4) Vdss (ml/kg) |
|---|---|---|---|---|
| iv 1a | 55.21 | 1.81 | 80 | 179 |
| 1b | 31.77 | 3.10 | 69 | 188 |
| 1c | 25.23 | 3.96 | 120 | 228 |
| 1d | 34.19 | 2.93 | 85 | 241 |
| mean | 36.60 | 2.95 | 89 | 209 |
| SD | 12.97 | 0.88 | 22 | 30 |
| sc 2a | 24.25 | | | |
| 2b | 21.67 | | | |
| 2c | 36.47 | | | |
| mean | 27.46 | | | |
| SD | 7.91 | | | |
| top 3a | 0.20 | | | |
| 3b | 0.80 | | | |
| 3c | 0.33 | | | |
| 3d | 0.14 | | | |
| mean | 0.37 | | | |
| SD | 0.30 | | | |
| sc + BPP 5a | 19.01 | | | |
| 5b | 23.60 | | | |
| 5c | 23.76 | | | |
| mean | 22.12 | | | |
| SD | 2.70 | | | |

| Route | 5) t1/2(1) (min) | 6) t1/2(2) (min) | 7) t1/2(3) (min) | 8) t1/2(Absp) (min) |
|---|---|---|---|---|
| iv 1a | 10.1 | 69.3 | 439 | |
| 1b | 5.8 | 51.1 | 168 | |
| 1c | 11.3 | 52.7 | 184 | |
| 1d | 6.5 | 63.3 | 325 | |

TABLE X-continued

| | | | | |
|---|---|---|---|---|
| mean | 8.4 | 59.1 | 279 | |
| SD | 2.7 | 8.7 | 128 | |
| sc 2a | | | | 45.6 |
| 2b | | | | 57.1 |
| 2c | | | | 85.9 |
| mean | | | | 62.9 |
| SD | | | | 20.8 |
| top 3a | | | | 55.8 |
| 3b | | | | 119.0 |
| 3c | | | | 37.1 |
| 3d | | | | 21.3 |
| mean | | | | 58.3 |
| SD | | | | 42.9 |
| sc + BPP 5a | | | | 75.2 |
| 5b | | | | 76.9 |
| 5c | | | | 131.0 |
| mean | | | | 94.4 |
| SD | | | | 31.7 |

| Route | 9) t1/2 (term)@ (min) | 10) Cpeak[a] (ng/ml) | 11) Tpeak* (min) | 12) BA[#] (%) |
|---|---|---|---|---|
| iv 1a | | | | |
| 1b | | | | |
| 1c | | | | |
| 1d | | | | |
| mean | | | | |
| SD | | | | |
| sc 2a | 73 | 95.30 | 120 | 66.4 |
| 2b | 72 | 59.90 | 180 | 62.0 |
| 2c | 176 | 73.40 | 240 | 99.7 |
| mean | 107 | 76.20 | 180 | 76.0 |
| SD | 60 | 17.80 | | 20.6 |
| top 3a | 479 | 0.26 | 240 | 0.6 |
| 3b | 1484 | 0.55 | 75 | 2.2 |
| 3c | 504 | 0.38 | 120 | 0.9 |
| 3d | 582 | 0.18 | 75 | 0.4 |
| mean | 762 | 0.34 | 98 | 1.0 |
| SD | 483 | 0.16 | | 0.8 |
| sc + BPP 5a | 229 | 40.80 | 240 | 51.9 |
| 5b | 266 | 58.40 | 420 | 61.5 |
| 5c | 490 | 25.80 | 420 | 64.9 |
| mean | 328 | 41.67 | 420 | 59.4 |
| SD | 141 | 16.32 | | 6.7 |

[a] mean peak serum concentration
* mean time for mean peak serum concentration
[#] bioavailability;
@ apparent terminal t1/2 for extravascular dose
SD = standard deviation
top = topical After completion of the pharmacokinetic experiments (12 hr.), the animals were sacrificed, and the reproductive tracts were removed and prepared for histological examination. Tissues were fixed in 10% NBF, embedded in paraffin, and stained with H&E and PAS/Alcian Blue dyes. Histologic sections of rabbit cervices were examined without knowledge of treatment group. For the purposes of this study the principal criteria evaluated were (1) relative compactness of the lamina propria and muscularis, (2) presence of giant cells, and (3) localization to the cervical region. The cervices were assigned to three categories: Positive, for loosely arranged lamina propria and underlying musulous with obvious increase in giant cells, Questionable, for some changes present but in less marked degree or noncervical location, and Negative, for cervix lacking changes.

The conclusion from the histological studies is that there was no clear association between treatment and histologic change.

Effect of Antioxidants and Co-solvents

This study is designed to assess the ability of various formulation adjuvants to stabilize relaxin in methylcellulose gel. Since the degradation occurs via photo-oxidation, antioxidants such as ascorbic acid and sodium metabisulfite were studied. In addition, because a possible source of free radicals is the peroxides on methylcellulose, co-solvents, such as glycerol and ethanol, were studied to determine if they would stabilize the formulation by decreasing the interaction between methylcellulose and relaxin. Finally, the effect of gel activation on relaxin oxidation by exposure of the gel to light prior to use in preparing the formulation was studied.

Gel Preparation: Four percent (w/v) methylcellulose gel was prepared by addition of 4 g of Methocel powder (Dow Chemical) to 100 ml of 10 mM citrate, pH5 buffer (made isotonic by NaCl). After the powder was dispersed into the buffer at 85° C., the solution was autoclaved at 121.5° C. for 30 minutes. Upon completion, a nitrogen head was placed over the gel and it was left overnight in the 5° C. incubator to hydrate. For formulations that contain glycerol and ethanol, the co-solvents were added directly to the formulation buffer. The "activated" gel was prepared by placing the autoclaved 4% gel in the fluorescent light box at 34° C. for 24 hours before being mixed with relaxin.

Study Protocol: Table XI lists the conditions, ingredients, and compositions in each formulation studied.

TABLE XI
Composition of Relaxin Formulations Used in This Study

| Formulation | Methylcellulose | Other Ingredient | Light Exposure |
|---|---|---|---|
| 1 | 3% | — | — |
| 2 | 3% | — | + |
| 3 | 3% | — | + |
| 4 | 3% | 0.5% ascorbic acid ascorbic acid stock (Aldrich Chem. Co.) | + |
| 5 | 3% | 0.2% metabisulfite (Fisher Scientific Corp) | + |
| 6 | 3% | 20% glycerol (Mallinckrodt) | |
| 7 | 3% | 20% ethanol (Mallinckrodt) | |
| 8 | 3% (activated) | — | — |

The relaxin solution was supplied at 1 mg/ml and concentrated to 2 mg/ml via an Amicon ultrafiltration unit. The samples were prepared by mixing the 2 mg/ml relaxin concentrate in pH 5 10 mM citrate buffer and 4% Methocel gel according to a volume ratio of 1:4. The solution and 4% gel were dispensed into two syringes separately, and the mixing was accomplished by pushing the contents across the syringes back and forth 20 times through an interlocking connector, as described above. Ascorbic acid and metabisulfite were incorporated in the relaxin solution prior to mixing with the gel. The final gel preparation was dispensed into autoclaved 1.5-ml glass HPLC vials in approximately 0.25-ml portions. The vials were capped, sealed, and placed upright into the 5° C. cold room under the fluorescent light. Samples in formulations #1 and #8 were wrapped in foil, while samples in formulation #3 were vacuumed briefly and refilled with nitrogen.

Degradation of relaxin in the gel was quantitated by RP-HPLC. Since the viscosity of the gel prevents direct application of samples to the HPLC, it was diluted 5-fold with formulation buffer prior to injection. The conditions of the chromatographic method were as follows:

Instrument: HP 1090L
Column: Vydac C4-300, 4.6×150 mm

Flow rate: 1 ml/min.
Wavelength: 214 nm
Injection volume: 200 μl
Temperature: Ambient
Mobile phase: (A) 0.1% TFA (B) 90% acetonitrile, 0.1% TFA
Gradient rate: 20% B increased to 50% B in 30 minutes
Results: Table XII lists the initial results of the study showing the percent main peak detected at respective time points.

TABLE XII

Relaxin Stability in Different Gel Formulations:
% Main Relaxin Peak at Various Time Points

| Formulation | % Main Peak | | |
|---|---|---|---|
| | T = 0 | T = 5 | T = 11 (days) |
| Control − light | 100 | 97 | 95.9 |
| Control + light | 98.7 | 33.3 | 0 |
| Control + light with N₂ head space | 99.1 | 38.6 | 0 |
| Control + light + ascorbic acid | 100 | 73 | 54.4 |
| Control + light + 20% glycerol | 100 | 95.5 | 89.4 |
| Control + light + 20% ethanol | 100 | 85 | 59.7 |
| Activated gel − light | 100 | 95.8 | 90.9 |

After 11 days the control that was protected from light retained 96% of its main peak area while the control exposed to light had completely degraded. Nitrogen head space did not retard the degradation. 0.5% ascorbic acid and 20% ethanol appeared to stabilize relaxin to approximately the same extent. At 11 days, the percentage of relaxin remaining was between 55 and 60%. The best result was obtained with the 20% glycerol formulation: 90% of the main peak was recovered after 11 days of light exposure. The "activated" gel sample exhibited a 9% loss in active protein, even when protected from light. Compared to the negative control (the plain gel formulation that was protected from light), it is evident that gel "activation" accelerated the degradation of the protein. This implies that excessive exposure to light is not recommended during the manufacture of the gel itself. The result from the formulation containing metabisulfite is not shown because the relaxin peak could not be detected in these samples and it was subsequently dropped from the study. It is possible that metabisulfite reacted with relaxin, resulting in total protein loss.

It is clear from these experiments that exposure to light played an essential role in initiating the degradation process. The inclusion of 20% glycerol in the formulation most effectively protected relaxin from light-induced oxidation. To a lesser extent, ascorbic acid and ethanol also stabilized the formulation. The effect of ethanol in this study may be underestimated, because a significant portion added may have been evaporated during the dispersion of methylcellulose powder. Combinations of glycerol, ethanol, and ascorbic acid may provide added stabilization.

The above results show that photo-oxidation of relaxin in methylcellulose gel can be effectively retarded by the incorporation of glycerol, ethanol, or ascorbic acid therein. A final formulation with acceptable shelf life may be designed by taking advantage of these adjuvants and protecting the product from excessive exposure to light.

We claim:

1. A biologically active stable, homogeneous pharmaceutical composition consisting essentially of an effective amount of human relaxin in a buffer which maintains the pH of the composition at about 4.5 to about 6 wherein said human relaxin essentially retains its physical stability and biological activity during storage of said composition at a temperature of about 5° C. for a period of at least two years.

2. The composition of claim 1 wherein the pH ranges from about 4.5 to about 5.5.

3. The composition of claim 2 wherein the pH is about 5.

4. The composition of claim 1 wherein the buffer is an organic acid buffer or histidine buffer.

5. The composition of claim 4 wherein the buffer is citrate or acetate buffer.

6. The composition of claim 1 having an ionic strength of at least 0.1 μ and having an osmolality of about 200 to 300 mmol/kg.

7. The composition of claim 6 having an ionic strength ranging from 0.1 to about 0.2 μ and having an osmolality of about 250 mmol/kg.

8. The composition of claim 7 having an ionic strength of about 0.15 μ.

9. The composition of claim 1 that is isotonic.

10. The composition of claim 9 comprising an alkali metal or alkaline earth metal salt or a sugar alcohol.

11. The composition of claim 10 comprising an alkali metal or alkaline earth metal halide or mannitol.

12. The composition of claim 11 comprising sodium chloride.

13. The composition of claim 12 wherein the buffer is citrate and the pH is about 5.

14. The composition of claim 12 wherein the buffer is acetate and the pH is about 5.

15. The composition of claim 1 further comprising a polyhydric sugar alcohol, ethanol, or polypropylene glycol.

16. The composition of claim 15 wherein the polyhydric sugar alcohol in glycerol.

17. The composition of claim 15 wherein the polyhydric sugar alcohol is selected from the group consisting of erythritol, glycerol, arabitol, xylitol, sorbitol, and mannitol.

18. The composition of claim 17 wherein the sugar alcohol is added in an amount of about 1 to 25% by weight based on the composition.

19. The composition of claim 18 wherein the sugar alcohol is added in an amount of about 2 to 5% by weight based on the composition.

20. The composition of claim 1 that is sterile.

21. The composition of claim 1 that is a liquid.

22. The composition of claim 20 that is frozen liquid.

23. The composition of claim 1 that is lyophilized.

24. A method of modulating the reproductive physiology of a mammal during pregnancy and parturition comprising administering to the mammal a therapeutically effective amount of the composition of claim 1.

25. The method of claim 24 wherein the mammal is human.

* * * * *

UNITED STATES PATENT AND TRADEMARK OFFICE
CERTIFICATE OF CORRECTION

PATENT NO. : 5,451,572
DATED : September 19, 1995
INVENTOR(S) : David C. Cipolla, et al It is certified that error appears in the above-indentified patent and that said Letters Patent is hereby corrected as shown below:

Column 28, line 57, claim 22, change "20" to --21--.

Signed and Sealed this

Fifth Day of March, 1996

*Attest:*

BRUCE LEHMAN

*Attesting Officer*     Commissioner of Patents and Trademarks